(12) United States Patent
Oldfield et al.

(10) Patent No.: US 6,669,935 B1
(45) Date of Patent: Dec. 30, 2003

(54) DELIVERY OF THERAPEUTIC AGENTS BY GENE THERAPY

(75) Inventors: Edward H. Oldfield, Philomont, VA (US); Zvi Ram, Tel Aviv (IL); Gerard J. McGarrity, Gaithersburg, MD (US)

(73) Assignees: The United States of America as represented by the Department of Health and Human Services, Washington, DC (US); Genetic Therapy, Inc., Gaithersburg, MD (US)

( * ) Notice: Subject to any disclaimer, the term of this patent is extended or adjusted under 35 U.S.C. 154(b) by 0 days.

(21) Appl. No.: 09/212,165

(22) Filed: Dec. 15, 1998

Related U.S. Application Data

(63) Continuation of application No. 08/371,530, filed on Jan. 17, 1995, now abandoned.

(51) Int. Cl.[7] .......................... A01N 63/00; A61K 48/00; C12N 15/63; C12N 15/86
(52) U.S. Cl. .................. 424/93.2; 435/320.1; 435/455; 435/456
(58) Field of Search .............................. 424/93.1, 93.2; 514/44; 435/320.1, 455, 456

(56) References Cited

FOREIGN PATENT DOCUMENTS

| EP | 476953 | 3/1992 |
|---|---|---|
| WO | WO93/04167 | 3/1993 |
| WO | WO93/10234 | 5/1993 |

OTHER PUBLICATIONS

Dang, V.C. et al. Gene therapy and translational cancer research. Clin. Cancer Res. 5:471–474, 1999.*
Wivel, N.A. & Wilson, J.M. Methods of gene delivery. Hematol. Oncol. Clin. North Am. 12:483–501, 1998.*
Eck, S.L. & Wilson, J.M. Gene–based therapy. Goodman & Gilman's The pharmacological basis of therapeutics, Ninth edition, pp. 77–101, 1996.*
Weyerbrock, A. & Oldfield, E.H. Gene transfer technologies for malignant gliomas. Curr. Opin. Oncol. 11:168–173, 1999.*
Rainov, G.N. et al. Intraarterial delivery of adenovirus vectors and liposome–DNA complexes to experimental brain neoplasms. Hum. Gen. Ther. 10:311–318, 1999.*

McCluskie et al. Route and method of delivery of DNA vaccine influence immune responses in mice and non–human primates. Mol. Med. 5:287–300, 1999.*
Ram, Z. et al. The effect of thymidine kinase transduction and ganciclovir therapy on tumor vasculature and growth of 9L gliomas in rats. J. Neurosurg 81:256–260, 1994.*
Lemarchand, P. et al. Adenovirus–mediated transfer of a recombinant human alpha 1–anti–trypsin cDNA to human endothelial cells. Proc. Natl. Acad. Sci. 89:6482–6486, 1992.*
Steg, P.G. et al. Arterial gene transfer to rabbit endothelial and smooth muscle cells using perc utaneous delivery of an adenoviral vector. Circulation 90:1648–1656, 1994.*
Palmer et al.; Genetically modified skin fibroblasts persist long after transplantation but gradually inactivate introduced genes, 1991, Proc. Natl. Acad. Sci. vol. 88: 1330–1334.*
Miller et al.; Targeted vectors for gene therapy, 1995, FASEB J. 9: 190–199.*
Verma et al.; Gene therapy–promises, problems and prospects, 1997, Nature vol. 389:239–242.*
Deonarain; LIgand–targeted receptor–mediated vectors for gene delivery, 1998, Exp. Opin. Ther. Patents 8(1): 53–69.*
Marshall; Gene Therapy's Growing Pains, 1995, Science vol. 269; 1050–1055.*
Short, et al., *Journal of Neuroscience Research*, vol. 27, pp. 427–439 (1990).
Ezzedine, et al., *New Biologist*, vol. 3, pp. 608–614 (1991).
Culver, et al., *Science*, vol. 256, pp. 1550–1552 (Jun. 1992).
Ram, et al., *Cancer Research*, vol. 53, pp. 83–88 (Jan. 1, 1993).
Neuwelt, et al., *Neurosurgery*, vol. 34, No. 4, pp. 777–784 (Apr. 1994).
Lowenstein, *Biotechnology*, vol. 12, pp. 1075–1079 (Nov. 1994).

* cited by examiner

*Primary Examiner*—David Guzo
*Assistant Examiner*—Quang Nguyen
(74) *Attorney, Agent, or Firm*—Klarquist Sparkman, LLP

(57) ABSTRACT

A process for treating a disease or disorder of a host by delivery of a therapeutic agent to the brain of the host, which comprises transducing endothelial cells of blood vessels located in the brain of a host in vivo with a vector including a polynucleotide encoding a therapeutic agent. The vector is administered intravascularly to the host, and the vector produces the therapeutic agent in the endothelial cells.

4 Claims, 19 Drawing Sheets

SEQUENCE OF THE MULTIPLE CLONING SITE IN THE pGI PLASMID

| 1/2 EcoRI | NotI | SnaBI | SalI | BamHI | XhoI | HindIII | ApaI |
|---|---|---|---|---|---|---|---|
| AATTC | GCGGCCGC | TACGTA | GTCGTA | GGATCC | CTCGAG | AAGCTT | GGGCCC |
| G | CGCCGGCG | ATGCAT | ATGCAT | CCTAGG | GAGCTC | TTCGAA | CCCGGG |

| 1/2ClaI | | | | | | | |
|---|---|---|---|---|---|---|---|
| AT | | | | | | | |
| TAGC | | | | | | | |

MAP OF nβ-GALACTOSIDASE CONSTRUCT

DELIVERY OF THERAPEUTIC AGENTS BY GENE THERAPY

Reference to Related Applications. This application is a continuation of U.S. patent application Ser. No. 08/371,530 filed on Jan. 17, 1995, now abandoned.

This invention relates to gene therapy for treatment of a disease or disorder by delivering therapeutic agents to the brain. More particularly, this invention relates to gene therapy through delivery of therapeutic agents to the brain by transducing endothelial cells of blood vessels located in the brain in vivo with a vector, wherein the vector is administered intravascularly. The invention further relates to treatment of tumors by transducing gene therapy wherein endothelial cells of blood vessels of the tumor are transduced with a polynucleotide expressing a therapeutic agent.

This invention further relates to the treatment of brain tumors by gene therapy wherein endothelial cells of blood vessels located in a brain tumor are transduced with a vector which includes a polynucleotide encoding an agent which when expressed provides for inhibition, prevention or destruction of the tumor. The vector is administered intravascularly. The agent may be a negative selective marker. Upon administration of an interaction agent to the host, the growth of the brain tumor is inhibited, prevented, or destroyed, thereby leading to regression of the tumor.

BACKGROUND OF THE INVENTION

Gene therapy has been used to deliver a therapeutic agent to the brain by in vivo transduction of cells which involves direct injection of a suitable vector into cells located in the brain, e.g., injection of the vector into tumor cells located in the brain.

There is a need for improved procedures for using gene therapy for delivering a therapeutic agent to the brain and in particular for the treatment of brain tumors by gene therapy which does not require direct introduction of a vector into the brain.

BRIEF DESCRIPTION OF THE DRAWINGS

The invention now will be described with respect to the drawings, wherein.

DETAILED DESCRIPTION OF THE INVENTION

Figure 1:
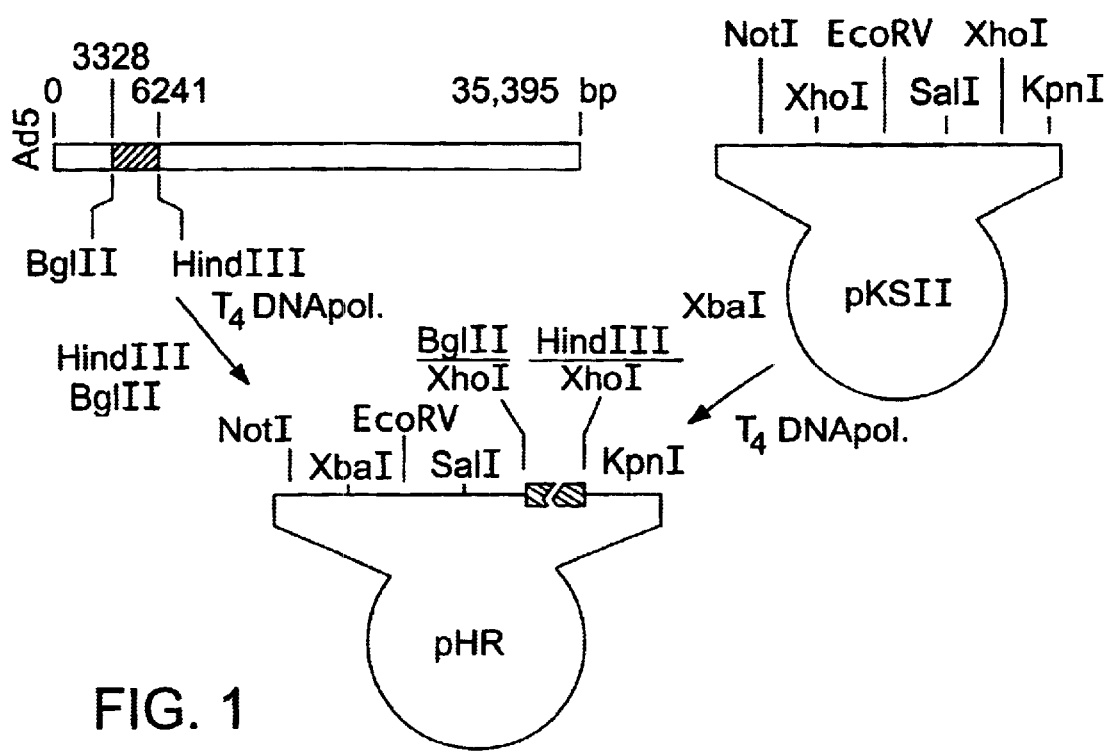
FIG. 1 is a schematic of the construction of plasmid pHR.

In accordance with an aspect of the present invention, there is provided a process for treating a disease or disorder of a host by delivery of a therapeutic agent to the brain of a host. The process comprises transducing endothelial cells of blood vessels located in the brain of a host in vivo with a vector including a polynucleotide encoding a therapeutic agent by administering intravascularly the vector to the host. The vector is one that transduces the endothelial cells of blood vessels located in the brain and expresses the therapeutic agent in such transduced cells.

The term "nucleic acid sequence" or "polynucleotide" as used herein means a DNA or RNA molecule, and includes polynucleotides encoding full length proteins and/or fragments of such full length proteins which can function as a therapeutic agent. The DNA may be genomic DNA or cDNA.

The term "therapeutic agent" is used in a generic sense and includes treating agents, prophylactic agents, and replacement agents.

Nucleic acid sequences encoding therapeutic agents which may be placed into the vector include, but are not limited to, nucleic acid sequences encoding tumor necrosis factor (TNF) genes, such as TNF-α; genes encoding interferons such as Interferon-α, Interferon-β, and Interferon-α; genes encoding interleukins such as IL-1, IL-1β, GMCSF, and Interleukins 2 through 14; gene encoding neurotransmitters; genes encoding neuromodulators; genes encoding neurohormones; genes encoding neurotropic factors; genes encoding endothelial growth factors (EGF's), such as vascular endothelial growth and permeability factor (VEGPF); genes encoding fibroblast growth factors (FGF's); genes encoding nerve growth factors (NGF's); the choline acetyl transferase (CAT) gene; the glial derived neurotrophic factor (GDNF) gene; genes encoding tyrosine hydroxylasation; genes encoding resistance to central nervous system infections; the PMP-22 gene; the FMR-1 gene; neuroprotective genes; genes encoding inhibitory signals that reduce brain excitability; the ornithine transcarbamylase (OTC) gene; and negative selective markers or "suicide" genes, such as viral thymidine kinase genes, such as the Herpes Simplex Virus thymidine kinase gene, the cytomegalovirus virus thymidine kinase gene, and the varicella-zoster virus thymidine kinase gene, or cytosine deaminase.

The method of the present invention may be employed to treat diseases or disorders of the brain and central nervous system. Such diseases and disorders include, but are not limited to, ischemic strokes, angiogenesis, metabolic diseases of the brain, axonal injury, Alzheimer's disease, Parkinson's disease, Huntington's disease, central nervous system infections, mucopolysaccharidoses (MPS, types I–VII), lipidoses (such as, for example, Gaucher's disease), Lesch-Nyhan syndrome, X-linked ADL, metachromatic leukodystrophy, Krabbe's disease, Charcot-Marie-Tooth disease, Fragile X, stroke, epilepsies, Down's syndrome, phenylketonuria, degenerative disorders, mental disorders, and a variety of disorders that can be affected by introducing a new compound or modifying the levels of existing proteins in the brain or nervous system.

For example, a vector including a gene encoding an endothelial growth factor (such as vascular endothelial growth and permeability factor) or fibroblast growth factor (FGF), may be administered intravascularly to a patient suffering from an ischemic stroke. In another example, a vector including a gene encoding nerve growth factor, or a gene encoding choline acetyl transferase, may be administered intravascularly to a patient suffering from Alzheimer's disease. Other genes which may be contained in the vectors, which are administered intravascularly to a patient, include, but are not limited to, genes encoding glial derived neurotrophic factor (GDNF), or tyrosine hydroxylasation for the treatment of Parkinson's disease; genes encoding resistance to central nervous system infections; the PMP-22 gene for treatment of Charcot-Marie-Tooth disease; the FMR-1 gene for treatment of Fragile X; neuroprotective genes to prevent further neuronal damage from stroke,; and genes encoding inhibitory signals that reduce brain excitability for treatment of epilepsy.

The vectors, upon intravascular administration, transduce endothelial cells located in blood vessels in the brain. In general, the vectors do not pass the blood brain barrier, or BBB, however, the therapeutic agent expressed by and secreted from the transduced endothelial cells passes the blood brain barrier whereby the therapeutic agent is delivered to brain cells.

The nucleic acid sequence encoding at least one therapeutic agent is under the control of a suitable promoter. Suitable promoters which may be employed include, but are not limited to, the gene's native promoter, retroviral LTR promoter, or adenoviral promoters, such as the adenoviral major late promoter; the cytomegalovirus (CMV) promoter; the Rous Sarcoma Virus (RSV) promoter; inducible promoters, such as the MMTV promoter; the metallothionein promoter; heat shock promoters; the albumin promoter; the histone promoter; the β-actin promoter; TK promoters; B19 parvovirus promoters; and the ApoAI promoter.

It is to be understood, however, that the scope of the present invention is not to be limited to specific foreign genes or promoters.

The polynucleotide which encodes a therapeutic agent generally will be in a vector which may be administered intravascularly to a host. The vectors are those that will transduce endothelial cells of blood vessels located in the brain and produce therein the therapeutic agent.

In one embodiment, the vector is a viral vector. Viral vectors which may be employed include RNA viral vectors (such as retroviral vectors), and DNA virus vectors (such as adenoviral vectors, adeno-associated virus vectors, and vaccinia virus vectors). When an RNA virus vector is employed, in constructing the vector, the polynucleotide encoding the therapeutic agent is in the form of RNA. When a DNA virus vector is employed, in constructing the vector, the polynucleotide encoding the therapeutic agent is in the form of DNA.

In one embodiment, the vector is an adenoviral vector.

The adenoviral vector which is employed may, in one embodiment, be an adenoviral vector which includes essentially the complete adenoviral genome. (Shenk, et al., *Curr. Top. Microbiol. Immunol.*, (1984); 111(3):1–39). Alternatively, the adenoviral vector may be a modified adenoviral vector in which at least a portion of the adenoviral genome has been deleted.

In one embodiment, the vector comprises an adenoviral 5' ITR; an adenoviral 3' ITR; an adenoviral encapsidation signal; a DNA sequence encoding a therapeutic agent; and a promoter for expressing the DNA sequence encoding a therapeutic agent. The vector is free of at least the majority of adenoviral E1 and E3 DNA sequences, but is not necessarily free of all of the E2 and E4 DNA sequences, and DNA sequences encoding adenoviral proteins transcribed by the adenoviral major late promoter.

In another embodiment, the gene in the E2a region that encodes the 72 kilodalton binding protein is mutated to produce a temperature sensitive protein that is active at 32° C., the temperature at which viral particles are produced, but is inactive at 37° C., the temperature of the animal or human host. This temperature sensitive mutant is described in Ensinger, et al., *J. Virology*, 10:328–339 (1972); Van der Vliet, et al., *J. Virology*, 15:348–354 (1975); and Friefeld, et al., *Virology*, 124:380–389 (1983); Englehardt, et al., *Proc.Nat.Acad.Sci.*, Vol. 91, pgs. 6196–6200 (June 1994); Yang, et al., *Nature Genetics*, Vol. 7, pgs. 362–369 (July 1994).

Such a vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. Such DNA segment serves as a substrate for homologous recombination with a modified or mutated adenovirus, and such segment may encompass, for example, a segment of the adenovirus 5 genome no longer than from base 3329 to base 6246 of the genome. The plasmid may also include a selectable marker and an origin of replication. The origin of replication may be a bacterial origin of replication. A representative example of such a shuttle plasmid is plasmid pAvS6, shown in FIG. 4. A desired DNA sequence encoding a therapeutic agent may be inserted into the multiple cloning site of such plasmid for production of a vector for use in accordance with the invention.

The plasmid is used to produce an adenoviral vector by homologous recombination with a modified or mutated adenovirus in which at least the majority of the E1 and E3 adenoviral DNA sequences have been deleted. Such homologous recombination may be effected through co-transfection of the plasmid vector and the modified adenovirus into a helper cell line, such as 293 cells, by $CaPO_4$ precipitation. The homologous recombination produces a recombinant adenoviral vector which includes DNA sequences derived from the shuttle plasmid between the Not I site and the homologous recombination fragment, and DNA derived from the E1 and E3 deleted adenovirus between the homologous recombination fragment and the 3' ITR.

In one embodiment, the homologous recombination fragment overlaps with nucleotides 3329 to 6246 of the adenovirus 5 genome (ATCC VR-5).

Through such homologous recombination, a vector is formed which includes an adenoviral 5' ITR, an adenoviral encapsidation signal; an E1a enhancer sequence; a promoter; a tripartite leader sequence; a DNA sequence encoding a therapeutic agent; a poly A signal; adenoviral DNA free of at least the majority of the E1 and E3 adenoviral DNA sequences; and an adenoviral 3' ITR. This vector may then be transfected into a helper cell line, such as the 293 helper cell line (ATCC No. CRL1573), which will include the E1a and E1b DNA sequences, which are necessary for viral replication, to generate replication defective viral vector particles.

The vector hereinabove described may include a multiple cloning site to facilitate the insertion of DNA sequence(s) encoding therapeutic agent(s) into the cloning vector. In general, the multiple cloning site includes "rare" restriction enzyme sites; i.e., sites which are found in eukaryotic genes at a frequency of from about one in every 10,000 to about one in every 100,000 base pairs. An appropriate vector is thus formed by cutting the cloning vector by standard techniques at appropriate restriction sites in the multiple cloning site, and then ligating the DNA sequence encoding a therapeutic agent into the cloning vector.

The DNA sequence encoding the therapeutic agent is under the control of a suitable promoter, which may be selected from those hereinabove described.

In one embodiment, the adenovirus may be constructed by using a yeast artificial chromosome (or YAC) containing an adenoviral genome according to the method described in Ketner, et al., *PNAS*, Vol. 91, pgs. 6186–6190 (1994), in conjunction with the teachings contained herein. In this embodiment, the adenovirus yeast artificial chromosome is produced by homologous recombination in vivo between adenoviral DNA and yeast artificial chromosome plasmid vectors carrying segments of the adenoviral left and right genomic termini. A DNA sequence encoding a therapeutic agent then may be cloned into the adenoviral DNA. The modified adenoviral genome then is excised from the adenovirus yeast artificial chromosome in order to be used to generate adenoviral vector particles as hereinabove described.

The adenoviral vector particles then may be administered intravascularly to a host. The host may be an animal host, including mammalian, non-human primate, and human hosts. The adenoviral particles, which are administered intravascularly, then transduce endothelial cells of blood vessels located in the brain.

The adenoviral particles are administered in an amount effective to produce a therapeutic effect in a host. In one embodiment, the adenoviral particles are administered in an amount of at least $1\times10^8$ plaque forming units (pfu), and in general such amount does not exceed about $2\times10^{12}$ plaque forming units, and preferably is from about $1\times10^{10}$ plaque forming units (pfu) to about $1\times10^{11}$ plaque forming units. The exact dosage of adenoviral particles to be administered is dependent upon a variety of factors, including the age, weight, and sex of the patient to be treated, and the nature and extent of the disease or disorder to be treated. The adenoviral particles may be administered as part of a preparation having a titer of adenoviral particles of at least $1\times10^{10}$ pfu/ml, and in general not exceeding $2\times10^{11}$ pfu/ml. The adenoviral particles may be administered in combination with a pharmaceutically acceptable carrier in a volume up to 10 ml.

In order to facilitate the transduction of the adenoviral vector particles into endothelial cells of blood vessels located in the brain, the adenoviral vector particles may be intravascularly administered to the host at a point in close proximity to the brain. The localizing of the intravascular administration is preferred in that such localization provides for improved transduction of cells in the area where required.

In a preferred embodiment, the vector is delivered to endothelial cells located in blood vessels in the brain by super selective angiography. Such procedure involves the use of an appropriate catheter and related devices (such as a guide wire). Through such a procedure, the catheter is directed into the carotid artery or vertebral artery to an appropriate point therein (preferably in close proximity to the brain) and the vector is administered into the artery through the catheter for transduction of endothelial cells of blood vessels located in the brain.

The adenoviral vector particles may be administered in combination with a pharmaceutically acceptable carrier suitable for administration to a patient, for example, a liquid carrier such as a saline solution, protamine sulfate (Elkins-Sinn, Inc., Cherry Hill, N.J.), or Polybrene (Sigma Chemical).

In another embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus. The vector is generally a replication incompetent retrovirus particle.

Retroviral vectors are useful as agents to mediate retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter. Alternatively, two genes may be expressed from a single promoter by the use of an Internal Ribosome Entry Site.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

In one embodiment, the retroviral vector may be one of a series of vectors based on the N2 vector containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point. In Moloney murine leukemia virus (MoMuLV), 5' to the authentic gag start, an open reading frame exists which permits expression of another glycosylated protein (pPr80$^{gag}$). Moloney murine sarcoma virus (MoMuSV) has alterations in this 5' region, including a frameshift and loss of glycosylation sites, which obviate potential expression of the amino terminus of pPr80$^{gag}$. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller, et al., *Biotechniques*, 7:980–990, 1989). Packaging-defective helper viruses for production of retroviral vectors are known in the art and examples thereof are described in Miller, Human Gene Therapy, Vol. 1, pgs. 5–14 (1990).

In one embodiment, the retroviral vector may be a Moloney Murine Leukemia Virus of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites. Such vectors are further described in U.S. patent application Ser. No. 919,062, filed Jul. 23, 1992, and incorporated herein by reference.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

The vector then is employed to transduce a packaging cell line to form a producer cell line. Examples of packaging cells which may be transfected include, but are not limited to, the PE501, PA317, ψ-2, ψ-AM, PA12, T19-14X, VT-19-17-H2, ψ CRE, ψ CRIP, GP+E-86, GP+envAm12, and DAN cell lines, as described in Miller, *Human Gene Therapy*, Vol. 1, pgs. 5–14 (1990). The vector containing the nucleic acid sequence encoding the therapeutic agent may transduce the packaging cells through any means known in the art. Such means include, but are not limited to, electroporation, the use of liposomes, and $CaPO_4$ precipitation.

The producer cells generate retroviral vector particles, which are administered to a host intravascularly, whereby such retroviral vector particles transduce endothelial cells of blood vessels located in the brain. The vectors then produce the therapeutic agent in the endothelial cells of the blood vessels located in the brain.

The retroviral vector particles are administered to the host in an amount effective to produce a therapeutic effect in the host. In general, the retroviral vector particles are administered in an amount of at least $1\times10^8$ colony forming units (cfu), and in general not exceeding $1\times10^{10}$ cfu, and preferably about $10^9$ cfu. The exact dosage of retroviral vector particles is dependent upon the factors hereinabove mentioned with respect to the adenoviral particles. The retroviral vector particles are administered as part of a preparation having a titer of retroviral vector particles of at least $1\times10^7$ cfu/ml and in general not exceeding $1\times10^9$ cfu/ml.

In one embodiment, the retroviral vector particles are introduced into the host by intravascularly administering the retroviral vector particles at a point in close proximity to the brain, e.g., by procedures hereinabove described.

The retroviral vector particles may be administered in combination with a pharmaceutically acceptable carrier, such as those hereinabove described with respect to the adenoviral vector particles, in a volume up to 10 ml.

The retroviral or adenoviral vector particles, upon intravascular administration, transduce endothelial cells located in blood vessels in the brain. The vectors do not passes the blood brain barrier, or BBB; however, in an embodiment of the invention the therapeutic agent expressed by and secreted from the transduced endothelial cells pass the blood brain barrier, whereby the therapeutic agent is delivered to brain cells. Thus, the method of the present invention may be employed to treat a variety of brain diseases and disorders, or non-brain diseases and disorders wherein the delivery of a therapeutic agent to the brain is effective for treating a disease in another part of the body.

For example, in a preferred aspect, the method of the present invention may be employed in treating brain tumors. Brain tumors develop their own vasculatures as they grow. Thus, such tumors may be treated by transducing endothelial cells located in blood vessels of a brain tumor by administering intravascularly (such as by administering via the carotid artery) to a host (preferably a human patient), a vector such as a retroviral vector or an adenoviral vector including a nucleic acid sequence encoding an agent which is capable of providing for the inhibition, prevention, or destruction of the growth of the tumor.

In accordance with a preferred embodiment of the present invention, the agent which is capable of providing for the inhibition, prevention, or destruction of the brain tumor upon expression of such agent is a negative selective marker; i.e., a material which in combination with a chemotherapeutic or interaction agent inhibits, prevents or destroys the growth of the brain tumor.

Thus, upon transduction of the endothelial cells of blood vessels located in a brain tumor with the negative selective marker, an interaction agent is administered to the human host. The interaction agent interacts with the negative selective marker in order to prevent, inhibit, or destroy the growth of the brain tumor.

Negative selective markers which may be employed include, but are not limited to, thymidine kinase, such as Herpes Simplex Virus thymidine kinase, cytomegalovirus thymidine kinase, and varicella-zoster virus thymidine kinase; and cytosine deaminase.

In one embodiment, the negative selective marker is a viral thymidine kinase selected from the group consisting of Herpes Simplex Virus thymidine kinase, cytomegalovirus thymidine kinase, and varicella-zoster virus thymidine kinase. When such viral thymidine kinases are employed, the interaction or chemotherapeutic agent preferably is a nucleoside analogue, for example, one selected from the group consisting of ganciclovir, acyclovir, and 1-2-deoxy-2-fluoro-β-D-arabinofuranosil-5-iodouracil (FIAU). Such interaction agents are utilized efficiently by the viral thymidine kinases as substrates, to produce a substance which is lethal to the endothelial cells of blood vessels located in a brain tumor expressing the viral thymidine kinases, thereby resulting in inhibition or destruction of the brain tumor.

In another embodiment, the negative selective marker is cytosine deaminase. When cytosine deaminase is the negative selective marker, a preferred interaction agent is 5-fluorocytosine. Cytosine deaminase converts 5-fluorocytosine to 5-fluorouracil, which is highly cytotoxic. Thus, the endothelial cells of blood vessels located in a brain tumor which express the cytosine deaminase gene convert the 5-fluorocytosine to 5-fluorouracil to inhibit the growth of and/or destroy the brain tumor.

The interaction agent is administered in an amount effective to inhibit, prevent, or destroy the growth of the tumor cells. For example, the interaction agent may be administered in an amount from about 5 mg to about 15 mg/kg of body weight, preferably about 10 mg/kg, depending on overall toxicity to a patient.

Although the invention is not to be limited thereby, it is believed that the endothelial cells of the blood vessels in the tumor are destroyed, and by destroying the vasculature of the tumor, one may effect ischemia and regression of the tumor. Such a method is a departure from the prior art in that previous gene therapy procedures for treating brain tumors involved direct introduction of a vector in the form of viral particles into the brain.

When a retroviral vector is employed, such retroviral vector will transduce more readily the endothelial cells of blood vessels located in the brain tumor because such endothelial cells replicate more rapidly than endothelial cells located in blood vessels of normal brain tissue. After the endothelial cells have been transduced with the retroviral vector, the patient is given an interaction agent, such as ganciclovir, aciclovir, 1-2-deoxy-2-fluoro-β-D-arabinofuranosil-5-iodouracil (FIAU), or 5-fluorocytosine, whereby the endothelial cells in the blood vessel of the brain tumor which have been transduced with the retroviral vector are killed. When an adenoviral vector including a negative selective marker is employed, the adenoviral vector will transduce the endothelial cells of the blood vessels located in the brain tumor, and may transduce healthy non-replicating cells as well; however, when the interaction agent, such as ganciclovir, is administered, only the endothelial cells of the blood vessels located in the brain tumor will be destroyed because healthy non-replicating cells which express TK are not affected by ganciclovir.

A further aspect of the present invention is directed to the treatment of tumors in general wherein endothelial cells of blood vessels located in a tumor of a host are transduced in vivo with a vector including a polynuceotide or nucleic acid sequence encoding an agent which is capable of providing for the inhibition, prevention, or destruction of the endothelial cells upon expression of the nucleic acid sequence encoding the agent. The vector produces the agent in the endothelial cells. In one embodiment, the vector is a viral vector such as those hereinabove described, and in particular, the viral vector may be an adenoviral vector or a retroviral vector selected from those hereinabove described.

Preferably, the agent which is capable of providing for the inhibition, prevention, or destruction of the tumor upon expression of such agent is a negative selective marker, which, in combination with a chemotherapeutic or interaction agent inhibits, prevents, or destroys the growth of the tumor. Such negative selective markers and interaction agents may be selected from those hereinabove described, and the vector and the interaction agent may be administered in amounts hereinabove described.

The vectors may be introduced into the endothelial cells of the blood vessels of a tumor by intravascular administration, i.e., through a vein or an artery. In one embodiment, the vectors may be administered to an artery at a point in close proximity to the tumor. Such administration may be effected, where appropriate, by directing a catheter into the artery to an appropriate point therein (preferably in close proximity to the tumor), and the vectors are administered into the artery through the catheter for transduction of the endothelial cells of blood vessels located in the tumor. As hereinabove noted, it is preferred to localize the introduction of the vector, e.g., by placing a catheter in close proximity to the tumor to be treated.

Tumors which may be treated in accordance with the present invention include malignant and non-malignant tumors.

Malignant (including primary and metastatic) tumors which may be treated include, but are not limited to, those occurring in the adrenal glands; bladder, bone; breast; cervix; endocrine glands (including thyroid glands, the pituitary gland, and the pancreas); colon; rectum; heart; hematopoietic tissue; kidney; liver; lung; muscle; nervous system; brain; eye; oral cavity; pharynx; larynx; ovaries; penis; prostate; skin (including melanoma); testicles; thymus; and uterus. The preferred tumors are those which are highly vascularized. In the case where a retroviral vector is used, the tumors preferably have a vasculature having rapidly dividing endothelial cells. It is to be understood, however, that the scope of the present invention is not to be limited to the treatment of any particular tumor.

EXAMPLES

The invention now will be described with respect to the following examples; however, the scope of the present invention is not intended to be limited thereby.

Example 1

Construction of Av1LacZ4

The adenoviral construction shuttle plasmid pAvS6 was constructed in several steps using standard cloning techniques including polymerase chain reaction based cloning techniques. First, the 2913 bp BglII, HindIII fragment was removed from Ad-d1327 and inserted as a blunt fragment into the XhoI site of pBluescript II KS⁻ (Stratagene, La Jolla, Calif.) (FIG. 1). Ad-d1327 (Thimmappaya, et al., *Cell*, Vol. 31, pgs. 543–551 (1983), incorporated herein by reference) is identical to Adenovirus 5 except that an XbaI fragment including bases 28591 to 30474 (or map units 78.5 to 84.7) of the Adenovirus 5 genome, and which is located in the E3 region, has been deleted. The complete Adenovirus 5 genome is registered as Genbank accession #M73260, incorporated herein by reference, and the virus is available from the American Type Culture Collection, Rockville, Md., U.S.A. under accession number VR-5.

Ad-d1327 was constructed by routine methods from Adenovirus 5 (Ad5). The method is outlined briefly as follows and previously described by Jones and Shenk, *Cell* 13:181–188, (1978). Ad5 DNA is isolated by proteolytic digestion of the virion and partially cleaved with XbaI restriction endonuclease. The XbaI fragments are then reassembled by ligation as a mixture of fragments. This results in some ligated genomes with a sequence similar to Ad5, except excluding sequences 28591 bp to 30474 bp. This DNA is then transfected into suitable cells (e.g. KB cells, HeLa cells, 293 cells) and overlaid with soft agar to allow plaque formation. Individual plaques are then isolated, amplified, and screened for the absence of the 1878 bp E3 region XbaI fragment.

The orientation of this fragment was such that the BglII site was nearest the T7 RNA polymerase site of pKSII⁻ and the HindIII site was nearest the T3 RNA polymerase site of pBluescript II KS⁻. This plasmid was designated pHR. (FIG. 1).

Figure 2:
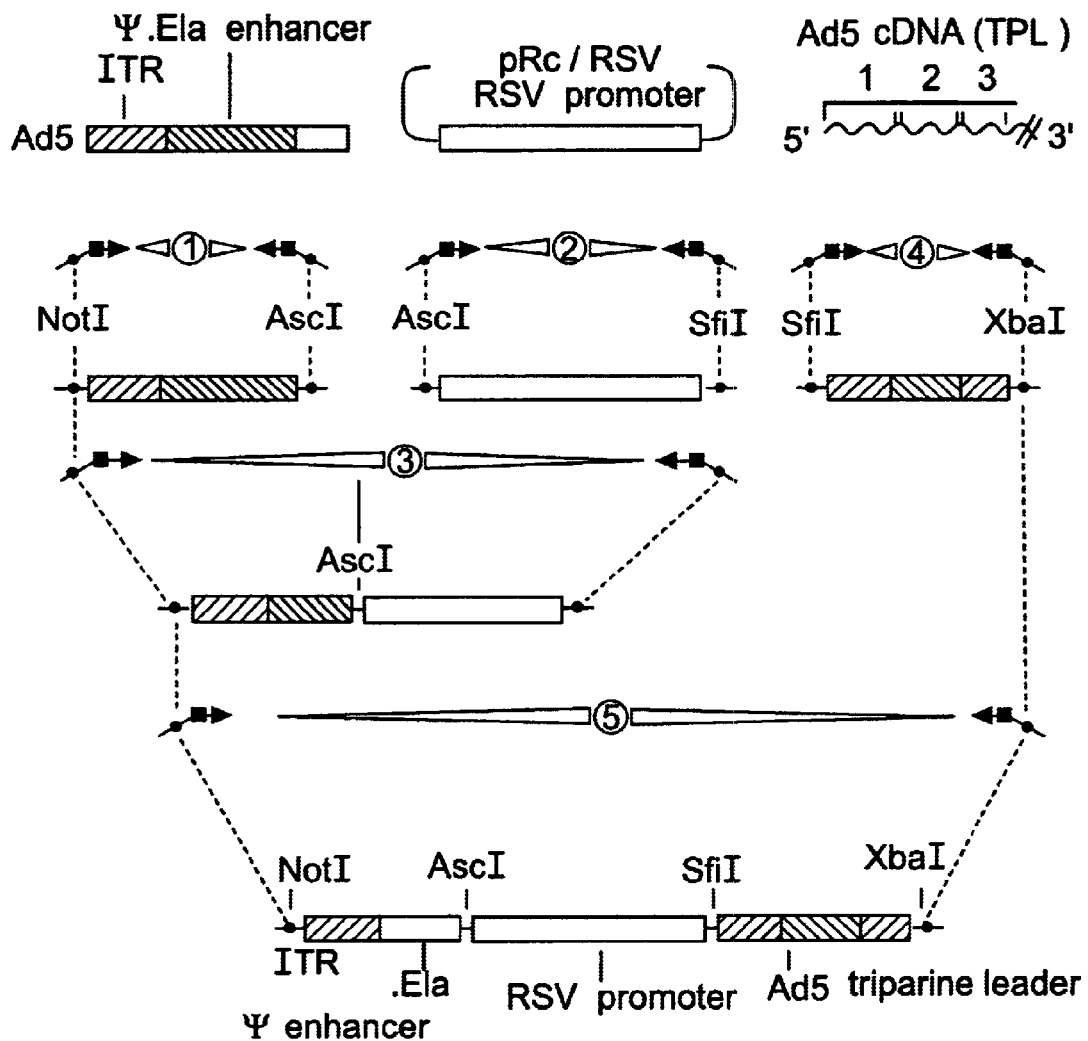
FIG. 2 is a schematic of the assembly of an adenoviral ITR, an encapsidation signal, a Rous Sarcoma Virus promoter, and an adenoviral tripartite leader sequence.

Second, the ITR, encapsidation signal, Rous Sarcoma Virus promoter, the adenoviral tripartite leader (TPL) sequence and linking sequences were assembled as a block using PCR amplification (FIG. 2). The ITR and encapsidation signal (sequences 1–392 of Ad-d1327 [identical to sequences from Ad5, Genbank accession #M73260], incorporated herein by reference) were amplified (amplification 1) together from Ad-d1327 using primers containing NotI or AscI restriction sites. The Rous Sarcoma Virus LTR promoter was amplified (amplification 2) from the plasmid pRC/RSV (sequences 209 to 605; Invitrogen, San Diego, Calif.) using primers containing an AscI site and an SfiI site. DNA products from amplifications 1 and 2 were joined using the "overlap" PCR method (amplification 3) (Horton, et al., *Biotechniques*, Vol. 8, pgs. 528–535 (1990)) with only the NotI primer and the SfiI primer. Complementarity between the AscI containing end of each initial DNA amplification product from reactions 1 and 2 allowed joining of these two pieces during amplification. Next the TPL was amplified (amplification 4) (sequences 6049 to 9730 of Ad-d1327 [identical to similar sequences from Ad5, Genbank accession #M73260]) from CDNA made from mRNA isolated from 293 cells (ATCC accession No. CRL 1573) infected for 16 hrs. with Ad-d1327 using primers containing SfiI and XbaI sites respectively. DNA fragments from amplification reactions 3 and 4 were then joined using PCR (amplification 5) with the NotI and XbaI primers, thus creating the complete gene block.

Third, the ITR-encapsidation signal-TPL fragment was then purified, cleaved with NotI and XbaI and inserted into the NotI, XbaI cleaved pHR plasmid. This plasmid was designated pAvS6A⁻ and the orientation was such that the NotI site of the fragment was next to the T7 RNA polymerase site (FIG. 3).

Figure 3:
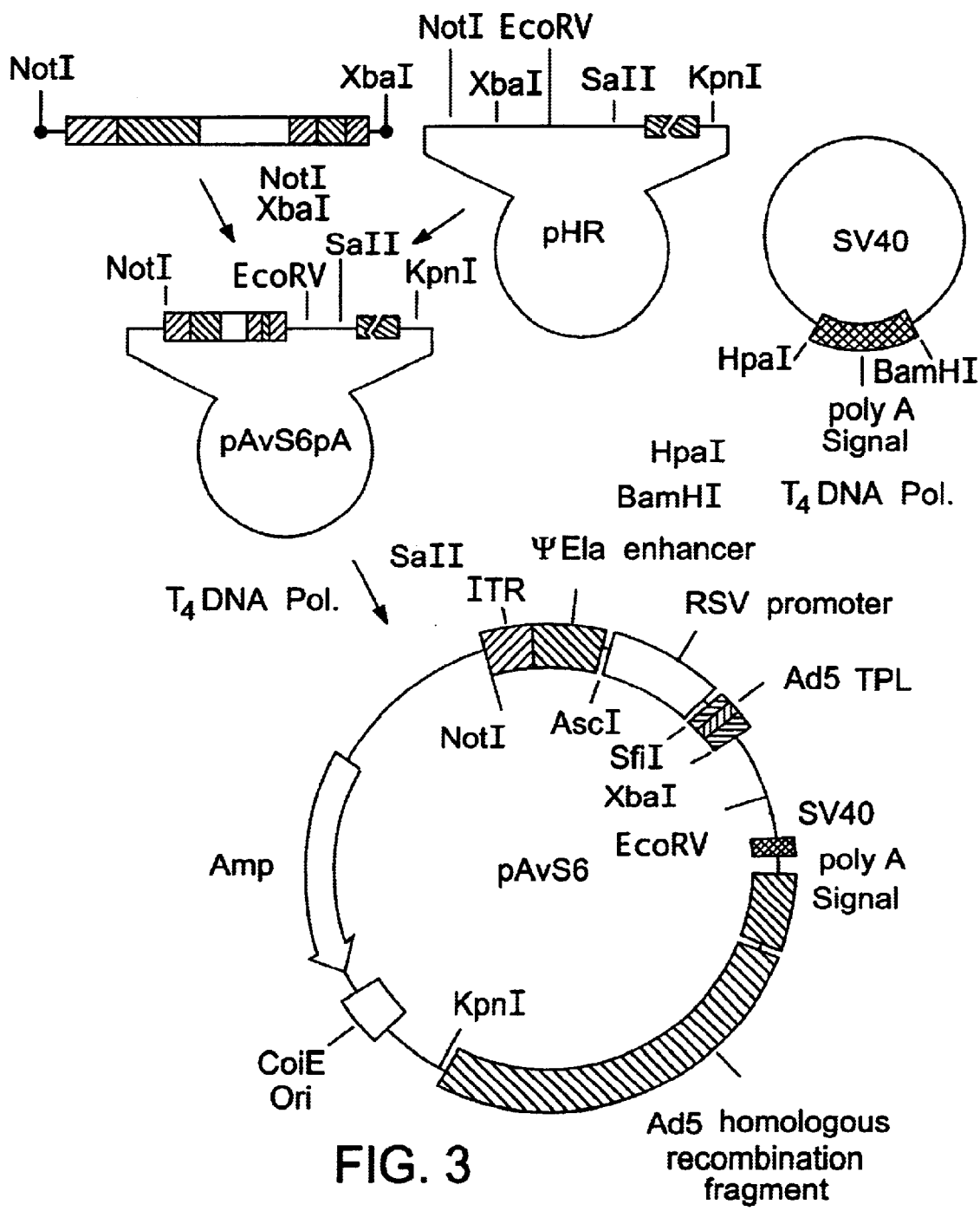
FIG. 3 is a schematic of the construction of plasmid pAvS6.
Figure 4:
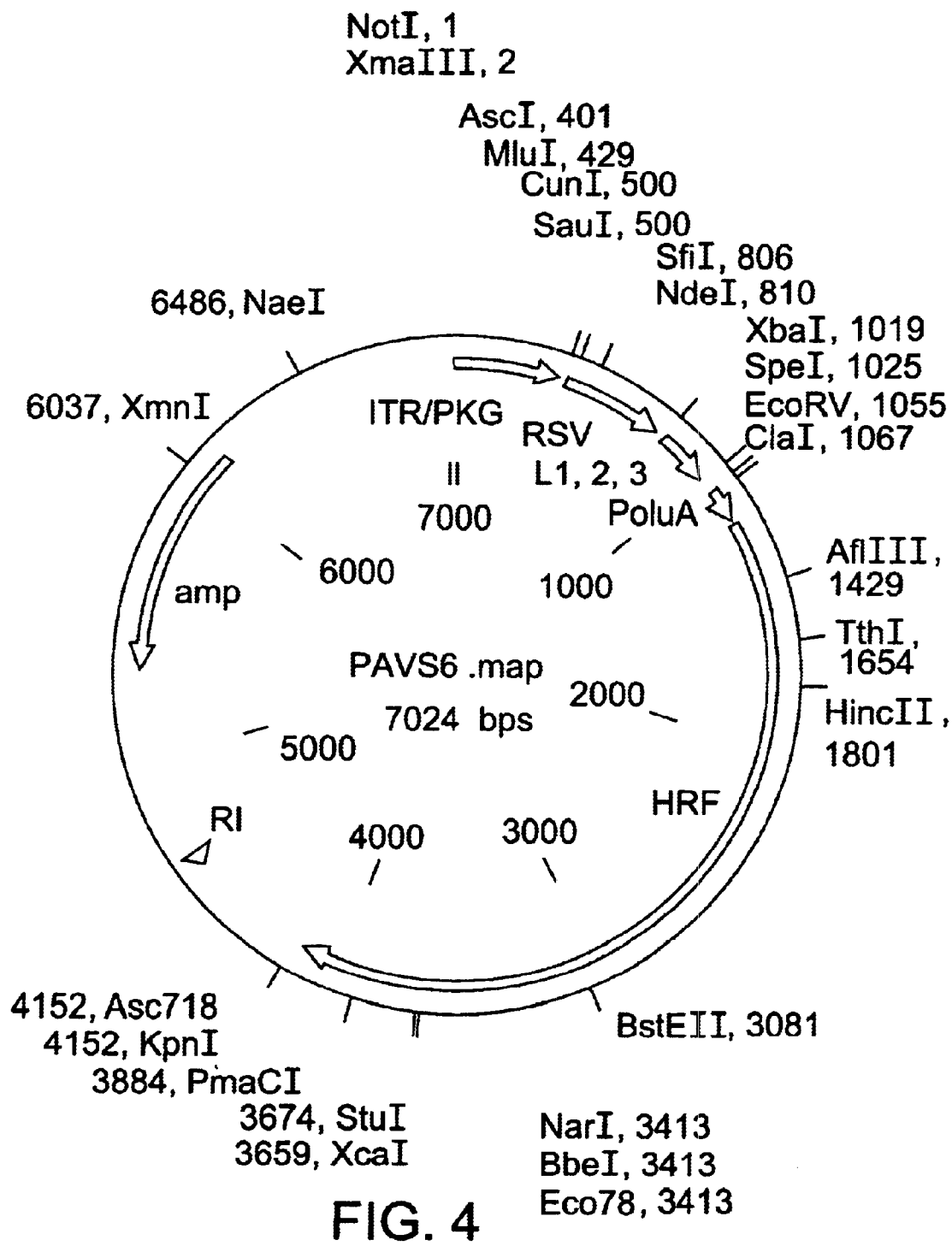
FIG. 4 is a map of plasmid pAvS6.

Fourth, the SV40 early polyA signal was removed from SV40 DNA as an HpaI-BamHI fragment, treated with T4 DNA polymerase and inserted into the SalI site of the plasmid pAvS6A-(FIG. 3) to create pAvS6 (FIGS. 3 and 4).

Figures 5, 8:
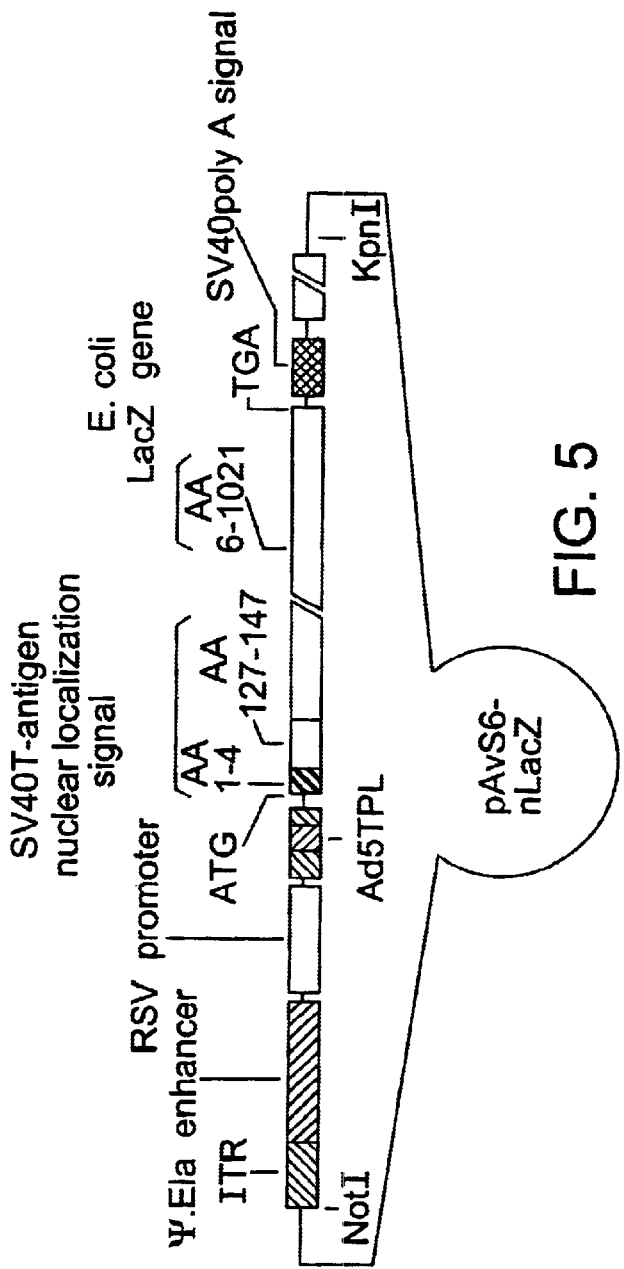
FIG. 5 is a map of plasmid pAvS6-nLacZ.
FIG. 8 is the sequence of the multiple cloning site of pG1.

The recombinant, replication-deficient adenoviral vector Av1LacZ4, which expresses a nuclear-targetable B-galactosidase enzyme, was constructed in two steps. First, a transcriptional unit consisting of DNA encoding amino acids 1 through 4 of the SV40 T-antigen followed by DNA encoding amino acids 127 through 147 of the SV40 T-antigen (containing the nuclear targeting peptide Pro-Lys-Lys-Lys-Arg-Lys-Val), followed by DNA encoding amino acids 6 through 1021 of *E. coli* B-galactosidase, was constructed using routine cloning and PCR techniques and placed into the EcoRV site of pAvS6 to yield pAvS6-nlacZ (FIG. 5).

The infectious, replication-deficient, Av1LacZ4 was assembled in 293 cells by homologous recombination. To accomplish this, plasmid pAvS6-nLacZ was linearized by cleavage with KpnI. Genomic adenoviral DNA was isolated from purified Ad-d1327 viruses by Hirt extraction, cleaved with ClaI, and the large (approximately 35 kb) fragment was isolated by agarose gel electrophoresis and purified. The ClaI fragment was used as the backbone for all first generation adenoviral vectors, and the vectors derived from it are known as Av1.

Figure 6:
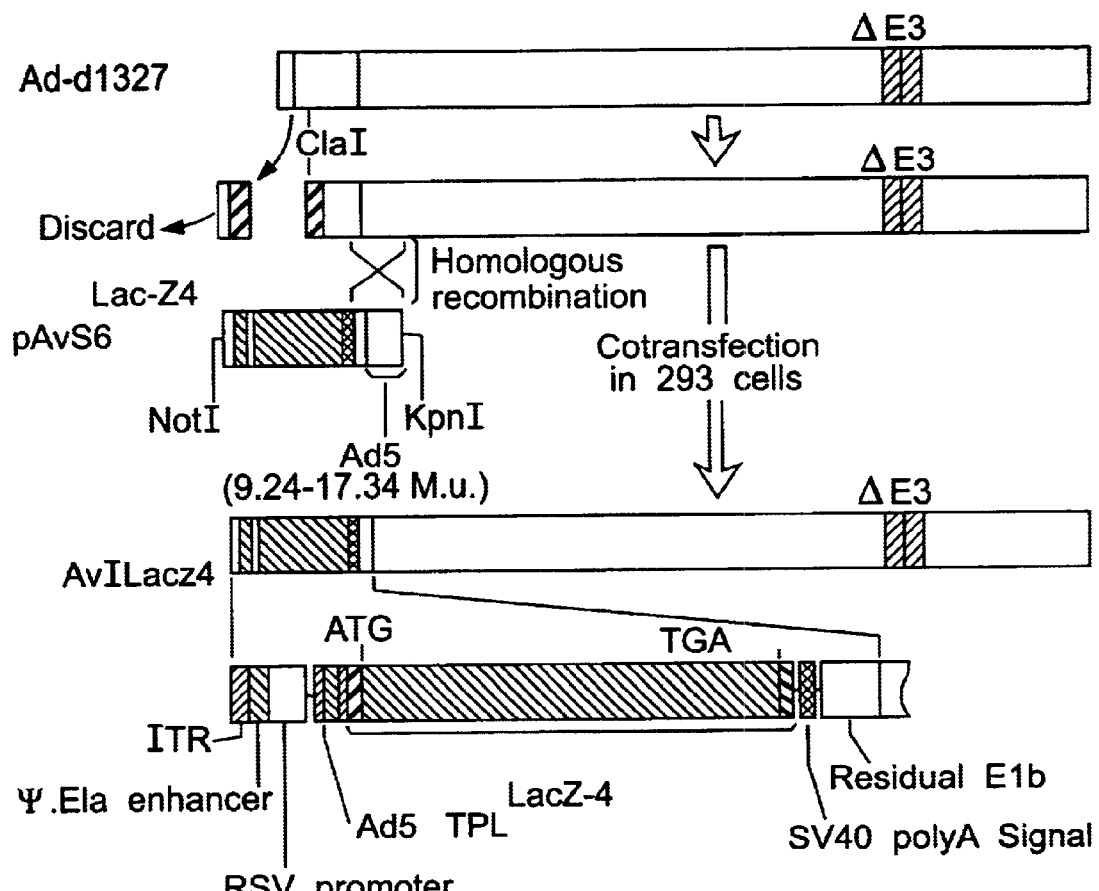
FIG. 6 is a map of Av1LacZ4.

Five micrograms of linearized plasmid DNA (pAvS6n-LacZ) and 2.5 μg of the large ClaI fragment of Ad-d1327 then were mixed and co-transfected into a dish of 293 cells by the calcium phosphate precipitation method. After 16 hours, the cells were overlaid with a 1:1 mixture of 2% Sea Plaque agar and 2×medium and incubated in a humidified, 37° C., 5% $CO_2$/air environment until plaques appeared (approximately one to two weeks). Plaques were selected and intracellular vector was released into the medium by three cycles of freezing and thawing. The lysate was cleared of cellular debris by centrifugation. The plaque (in 300 μl) was used for a first round of infection of 293 cells, vector release, and clarification as follows:

One 35 mm dish of 293 cell was infected with 100 μl of plaque lysate plus 400 μl of IMEM-2 (IMEM plus 2% FBS, 2 mM glutamine (Bio Whittaker 046764)) plus 1.5 ml of IMEM-10 (Improved minimal essential medium (Eagle's) with 2×glutamine plus 10% vol./vol. fetal bovine serum plus 2 mM supplemental glutamine (Bio Whittaker 08063A) and incubated at 37° C. for approximately three days until the cytopathic effect, a rounded appearance and "grapelike" clusters, was observed. Cells and supernatant were collected as a crude viral lysate. Av1LacZ4 vector (a schematic of the construction of which is shown in FIG. 6) was released by five cycles of freeze/thawing. The crude viral lysate was centrifuged in an ultracentrifuge (Beckman XL-80) at 7,000 rpm, 4° C. for 10 minutes to remove cellular debris. The resultant supernatant was layered onto a CsCl gradient composed of equal volumes of 1.25 g/ml and 1.40 g/ml CsCl solutions. The gradient was centrifuged in an SW40Ti rotor of the Beckman ultracentrifuge at 35,000 rpm, 20° C. for 1 hour. The recovered intact viral vector was subjected to a second round of banding in 1.33 g/ml CsCl solution at 35,000 rpm, 20° C. for 1 hour. The intact vectors were dialyzed and stored at −70° C. with the addition of 10% glycerol until used. Av1LacZ4 also is described in Yei, et al., *Human Gene Therapy*, Vol. 5, pgs. 731–744 (1994); Trapnell, *Advanced Drug Delivery Reviews*, Vol. 12, pgs. 185–199 (1993), and Smith, et al., *Nature Genetics*, Vol. 5, pgs. 397–402 (December 1993), which are incorporated herein by reference.

Example 2

Construction of G1nBgSvNa

Figure 7:
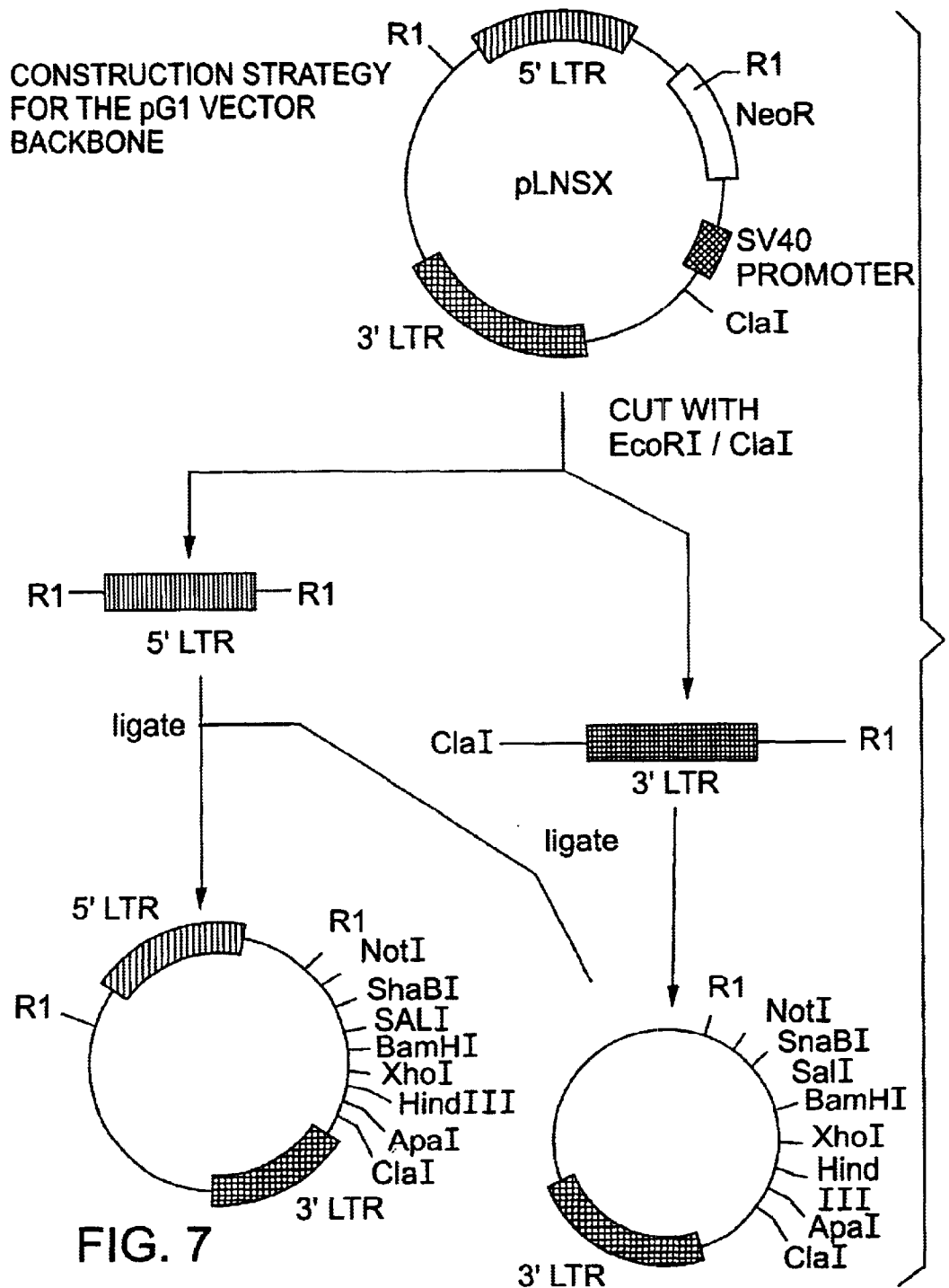
FIG. 7 is a schematic of the construction of plasmid pG1.
Figure 9:
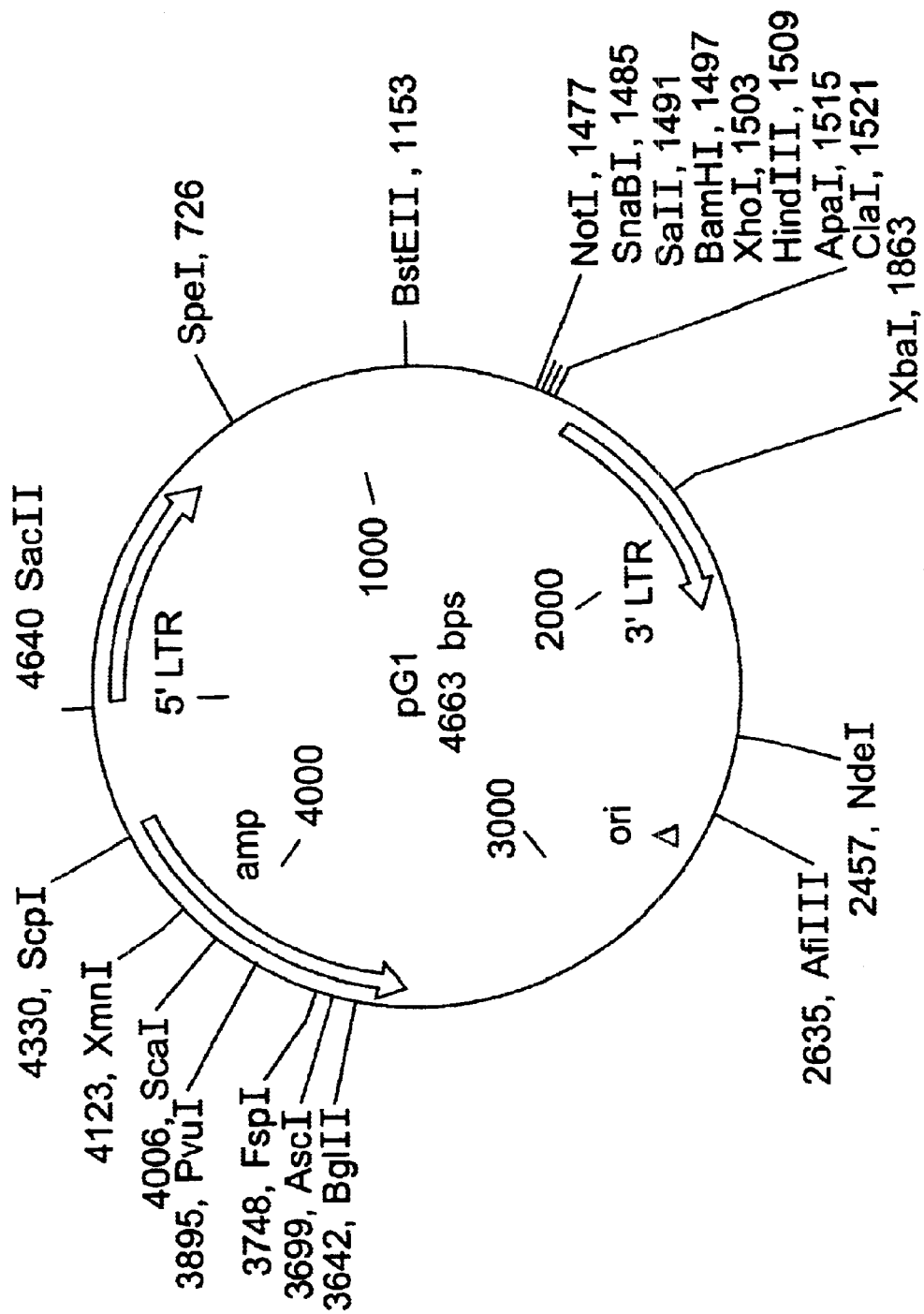
FIG. 9 is a map of plasmid pG1 (SEQ ID NOS: 6–7)

Plasmid pG1nBgSvNa was derived from plasmid pG1. Plasmid pG1 was constructed from PLNSX (Palmer, et al., *Blood*, Vol. 73, pgs. 438–445). The construction strategy for plasmid pG1 is shown in FIG. 7. The 1.6 kb EcoRI fragment, containing the 5' Moloney Murine Sarcoma Virus (MoMuSV) LTR, and the 3.0 kb EcoRI/ClaI fragment, containing the 3' LTR, the bacterial origin of replication and the ampicillin resistance gene, were isolated separately. A linker containing seven unique cloning sites was then used to close the EcoRI/ClaI fragment on itself, thus generating the plasmid pGO. The plasmid pGO was used to generate the vector plasmid pG1 (FIG. 9) by the insertion of the 1.6 kB EcoRI fragment containing the 5' LTR into the unique EcoRI site of pGO. Thus, pG1 (FIG. 9) consists of a retroviral vector backbone composed of a 5' portion derived from MoMuSV, a short portion of gag in which the authentic ATG start codon has been mutated to TAG (Bender, et al. 1987), a 54 base pair multiple cloning site (MCS) containing, from 5' to 3' the sites EcoRI, NotI, SnaBI, SalI, BamHI, XhoI, HindII, ApaI, and ClaI and a 3' portion of MoMuLV from base pairs 7764 to 7813 (numbered as described (Van Beveren, et al., *Cold Spring Harbor*, Vol. 2, pg. 567, 1985) (FIG. 8). The MCS was designed to generate a maximum number of unique insertion sites, based on a screen of non-cutting restriction enzymes of the pG1plasmid, the $neo^r$ gene, the β-galactosidase gene, the $hygromycin^r$ gene, and the SV40 promoter.

Figure 10:
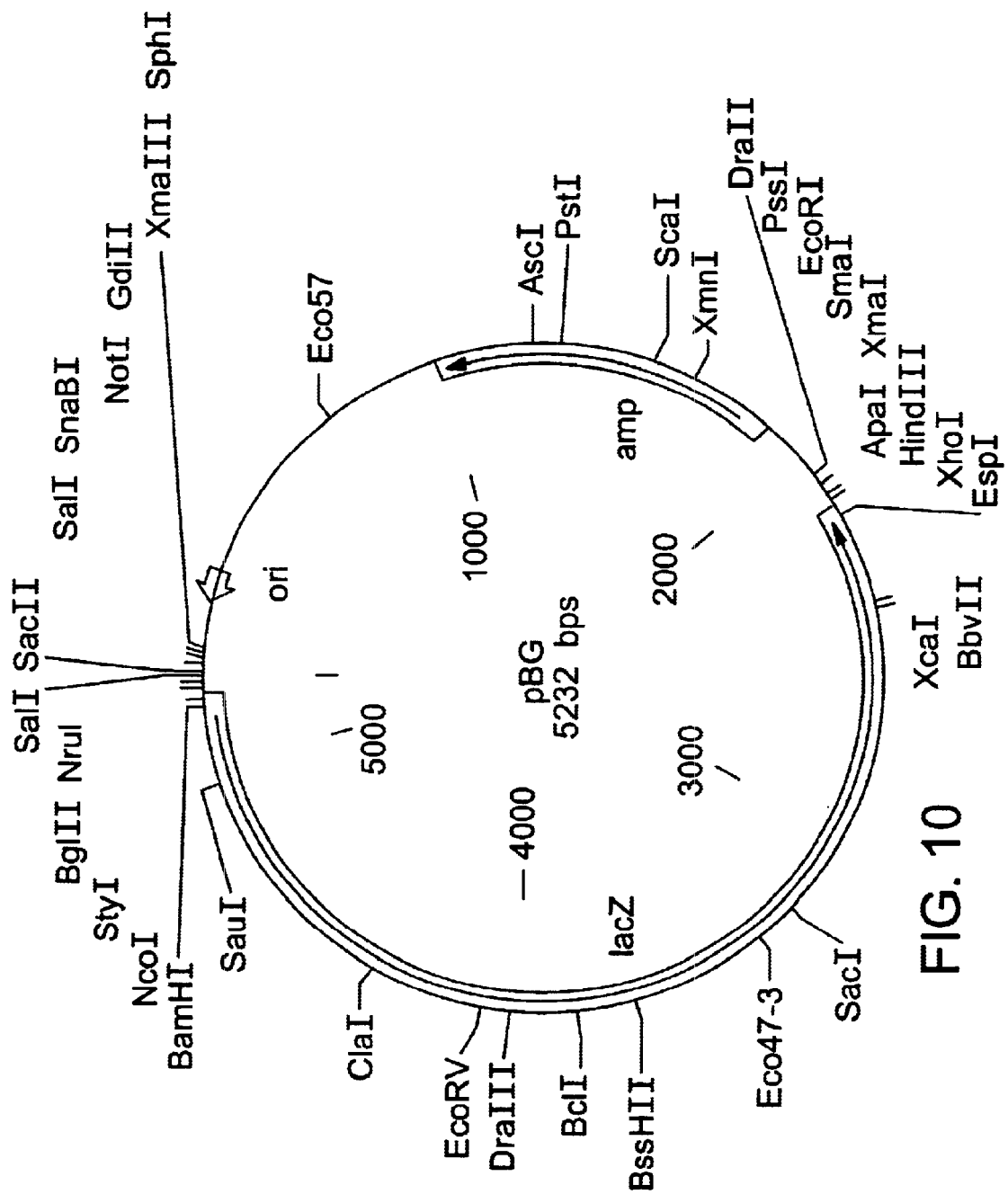
FIG. 10 is a map of plasmid pBg.

To construct pBg (FIG. 10) the 3.0 kb BamHI/EcoRI lacZ fragment that encodes β-galactosidase was isolated from pMC1871 (Pharmacia). This fragment lacks the extreme 5' and 3' ends of the β-galactosidase open reading frame. Linkers that would restore the complete lacZ open reading frame and add restriction sites to each end of the lacZ gene were synthesized and ligated to the BamHI/EcoRI lacZ fragment. The structure of the 5' linker was as follows: 5'-½ NedI-SphI-NotI-SnaBI-SalI-SacII-AccI-NruI-BglII-III 27 bp ribosomal binding signal-Kozak consensus sequence/NcoI-first 21 bp of the lacZ open reading frame-½ BamHI-3'. The structure of the 3' linker was as follows: 5'-½mutated EcoRI-last 55 bp of the lacZ open reading frame-XhoI-HindIII-SmaI-½ EcoRI-3'. The restriction sites in the linkers were chosen because they are not present in the neomycin resistance gene, the β-galactosidase gene, the hygromycin resistance gene, or the SV40 promoter The 27 bp ribosomal binding signal was included in the 5' linker because it is believed to enhance mRNA stability (Hagenbuchle, et al., *Cell* 13:551–563, 1978 and Lawrence and Jackson, *J. Mol. Biol.* 162:317–334, 1982) The Kozak consensus sequence (5'-GCCGCCACCATGG-3', SEQ ID NO: 1) has been shown to signal initiation of mRNA translation (Kozak, *Nucl. Acids Res.* 12:857–872, 1984). The Kozak consensus sequence includes the NcoI site that marks the ATG translation initiation codon.

pBR322 (Bolivar et al., *Gene* 2:95, 1977) was digested with NdeI and EcoRI and the 2.1 kb fragment that contains the ampicillin resistance gene and the bacterial origin of replication was isolated. The ligated 5' linker-lacZ-3' linker DNA described above was ligated to the pBR322 NdeI/EcoRI vector to generate pBg. pBg has utility as a shuttle plasmid because the lacZ gene can be excised and another gene inserted into any of the restriction sites that are present at the 5' and 3' ends of the lacZ gene. Because these restriction sites are reiterated in the pG1 plasmid, the lacZ gene or genes that replace it in the shuttle plasmid construct can easily be moved into pG1.

Figure 11:
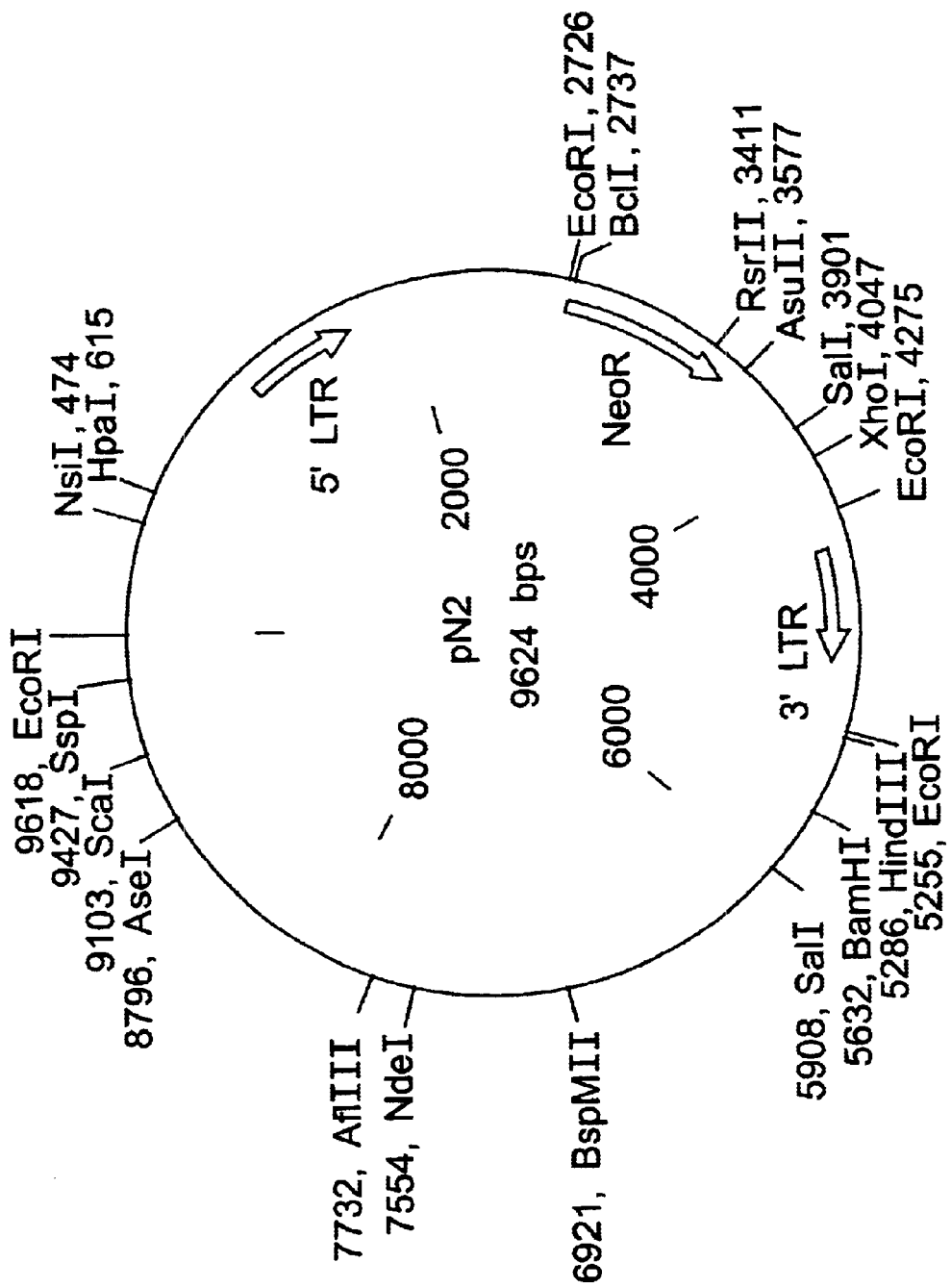
FIG. 11 is a map of plasmid pN2.
Figure 12:
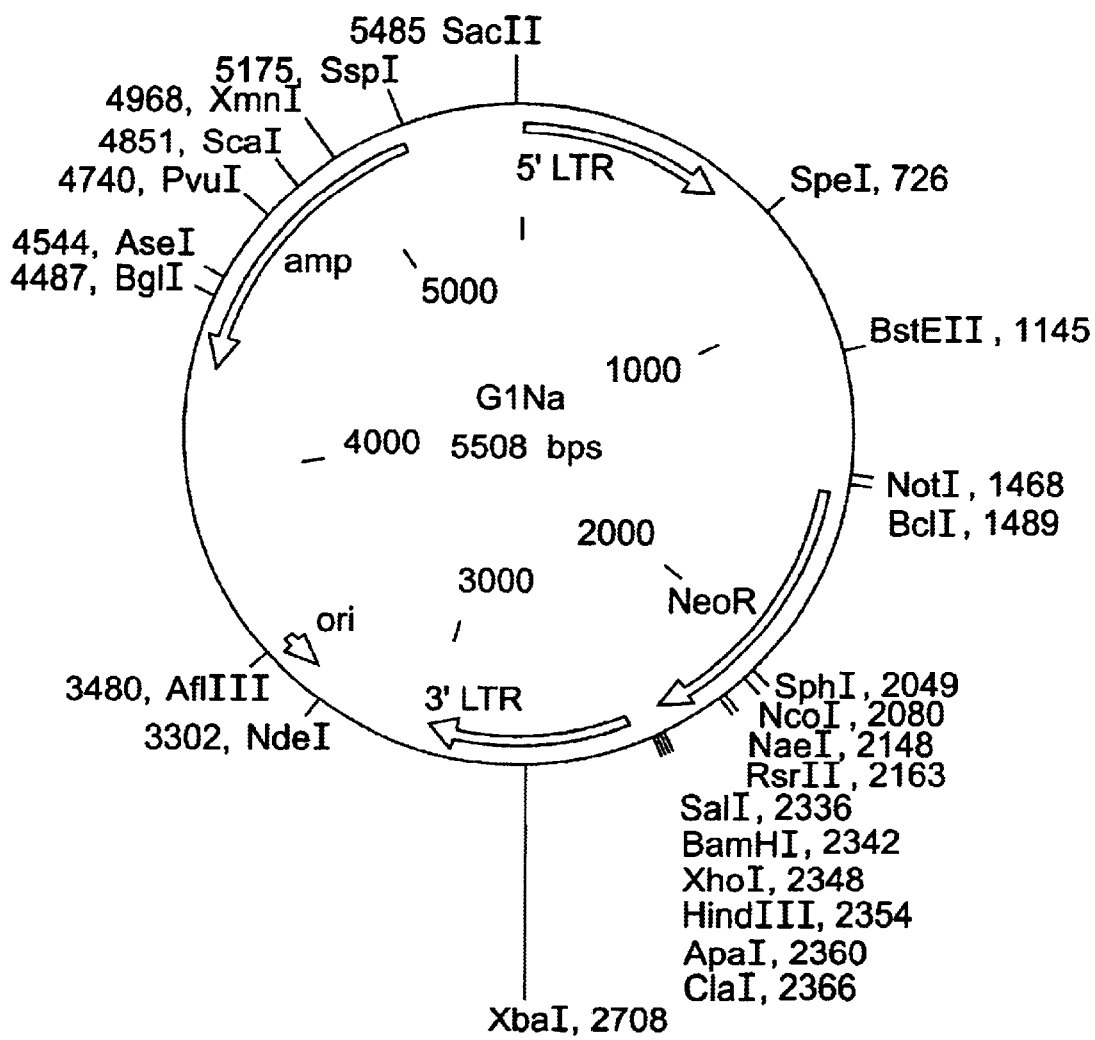
FIG. 12 is a map of plasmid pG1Na.
Figure 13:
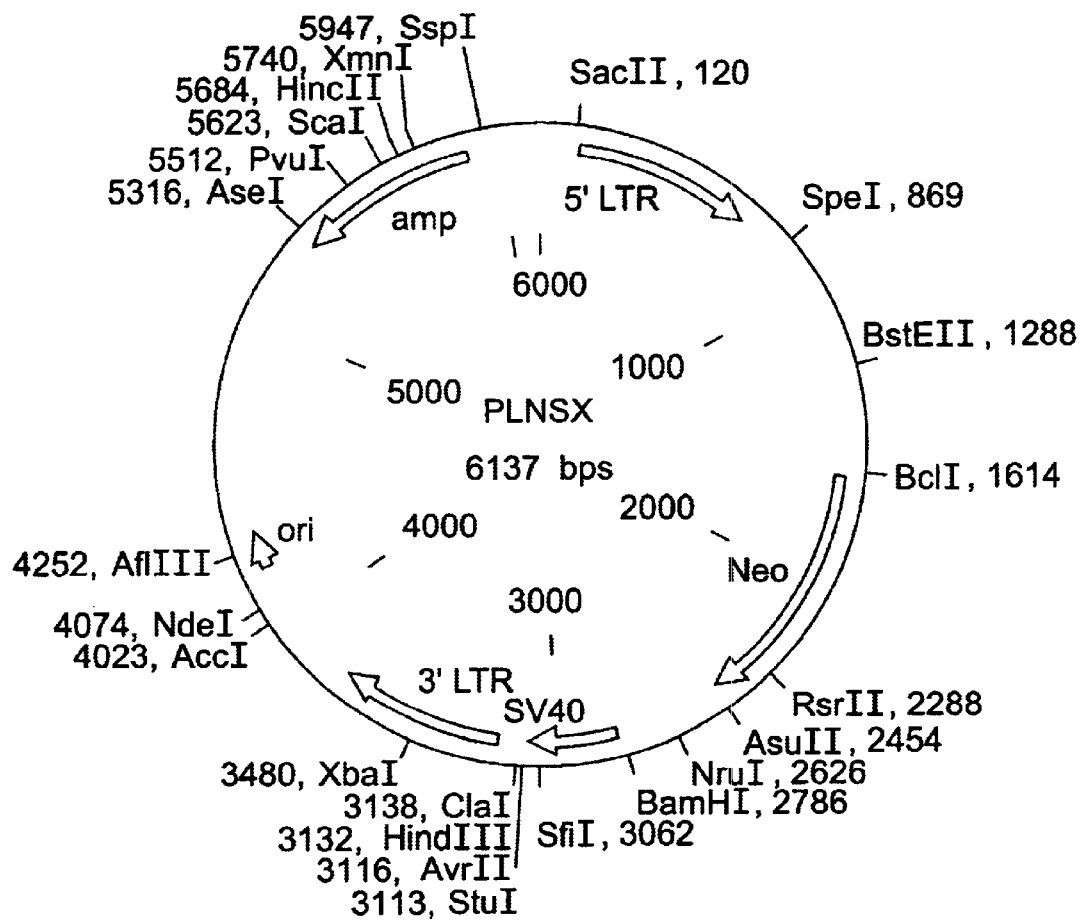
FIG. 13 is a map of plasmid pLNSX.
Figure 14:
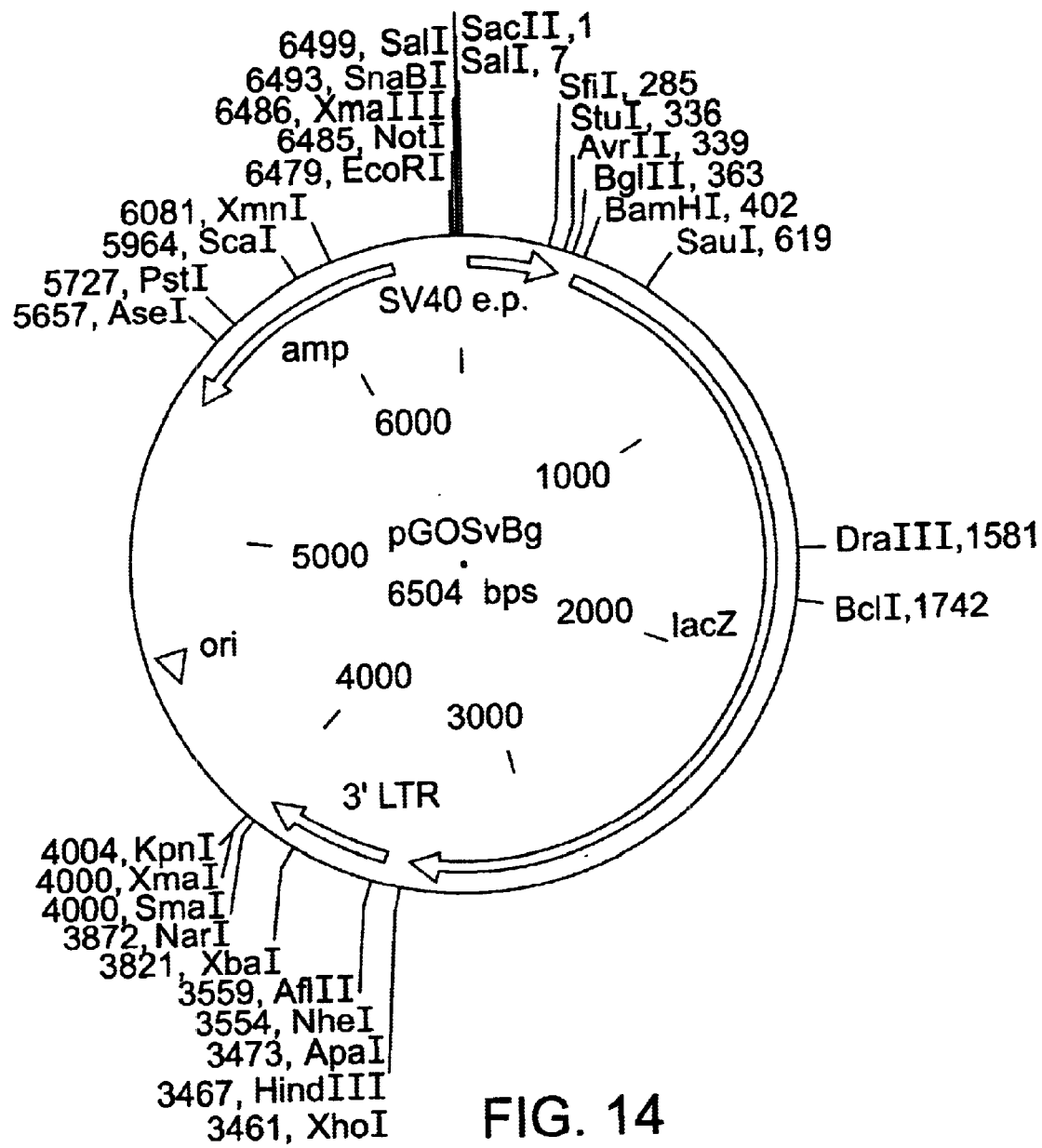
FIG. 14 is a map of plasmid pGOSvBg.
Figure 15:
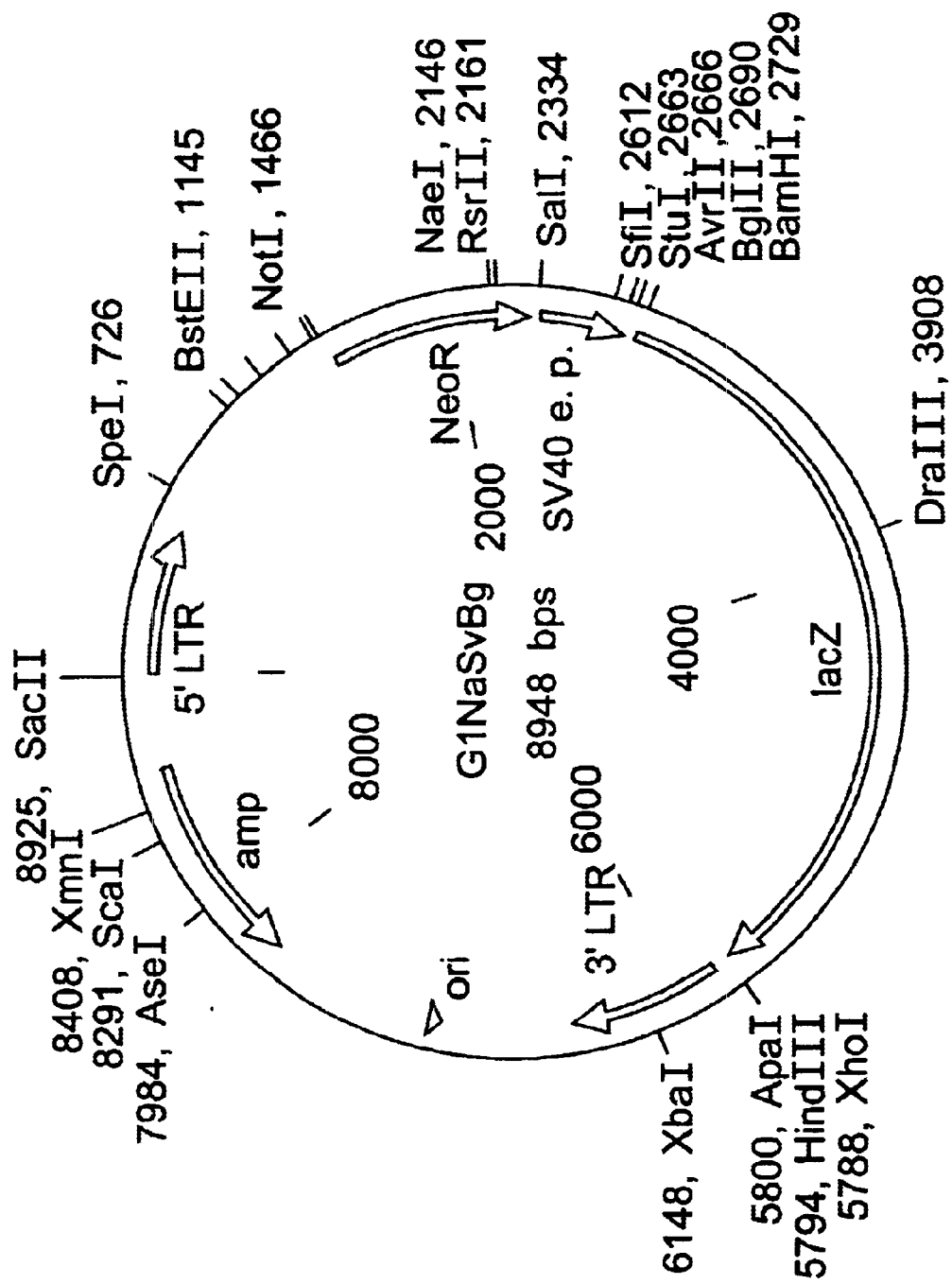
FIG. 15 is a map of plasmid pG1NaSvBg.
Figure 16:
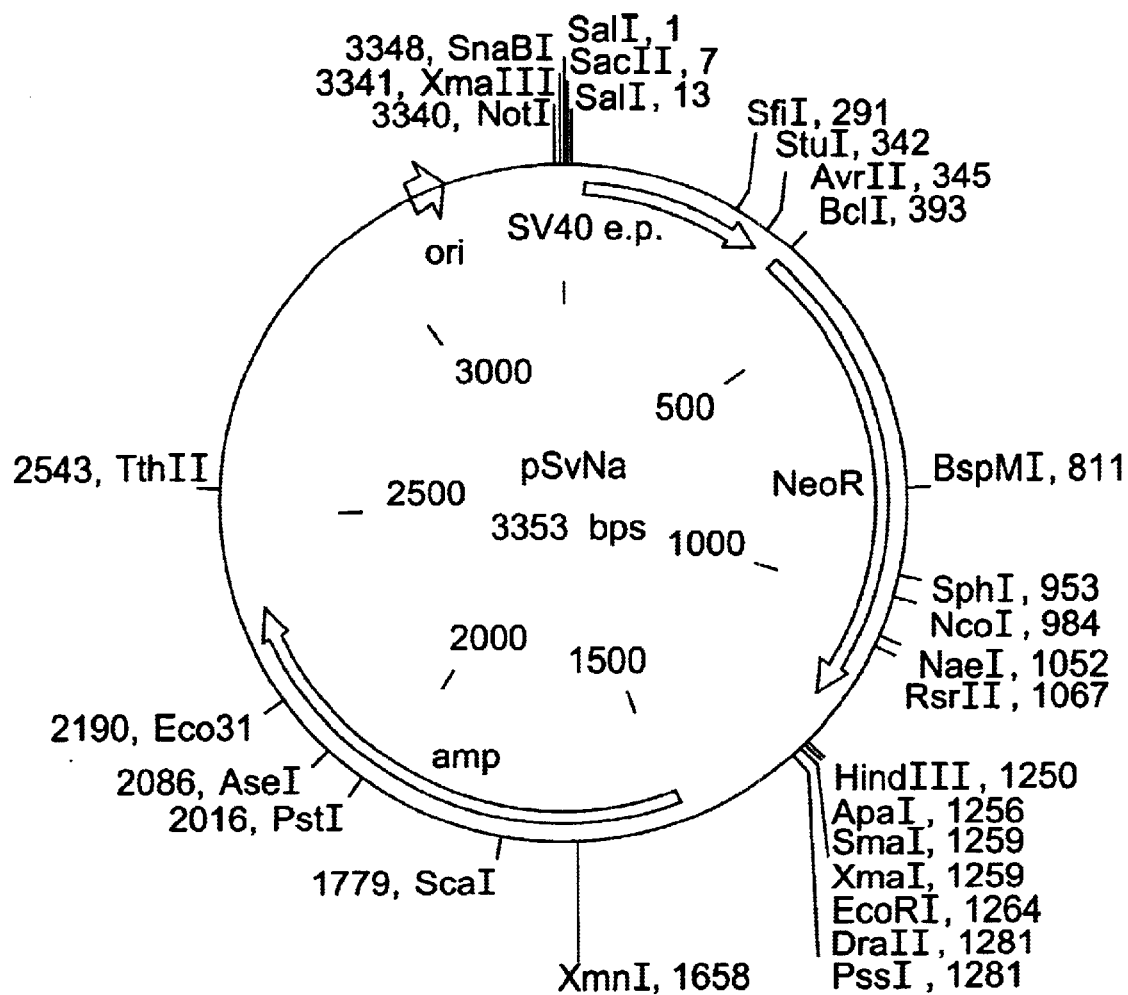
FIG. 16 is a map of plasmid pSvNa.
Figure 17:
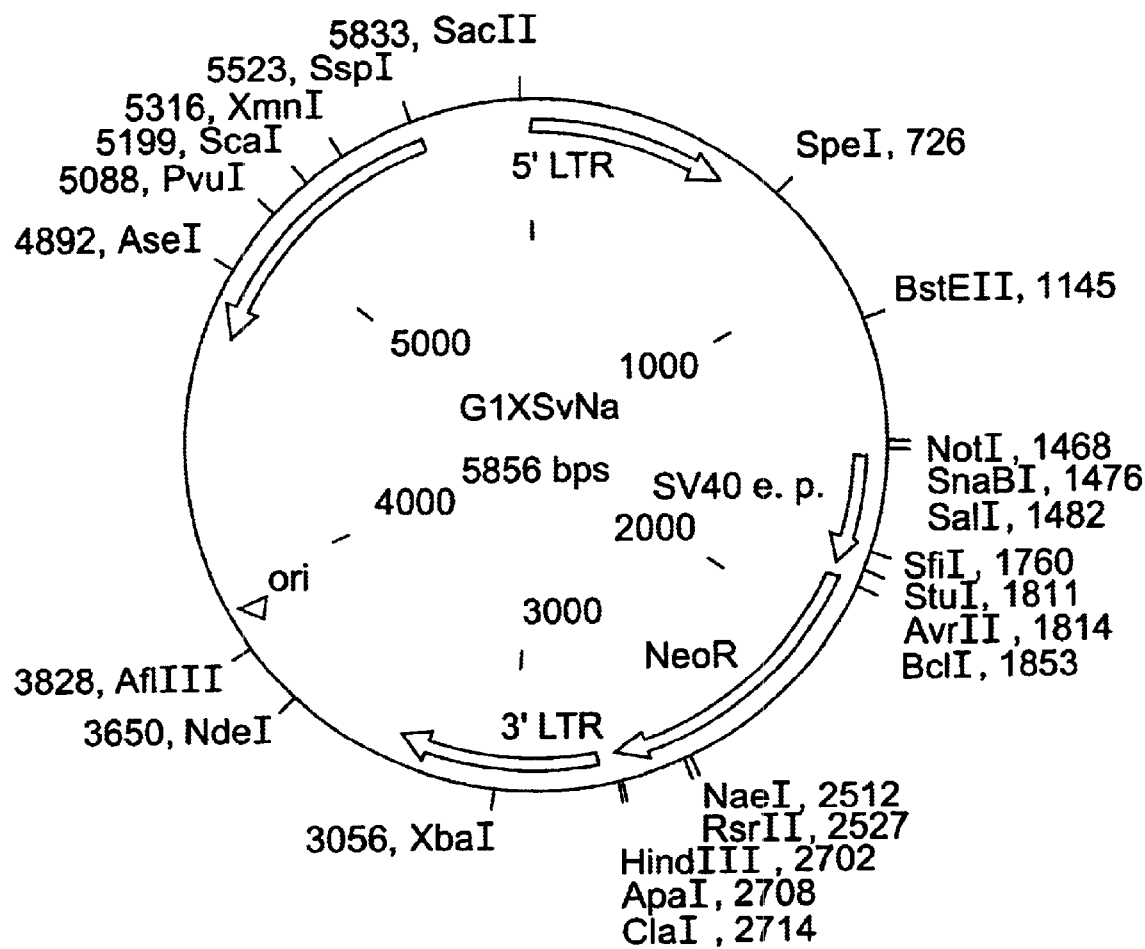
FIG. 17 is a map of plasmic pG1XSvNa.

The "backbone" vector pG1Na was constructed from pG1 and pN2 (Armentano, et al., *J. Virology*, Vol. 61, pgs. 1647–1650 (1987)). pG1Na was constructed by cutting pN2 (FIG. 11) with EcoRI and AsuII, filling in the ends of the EcoRI/AsuII fragment containing the $neo^R$gene, and ligating the fragment into SnaBI digested pG1 to form pG1Na (FIG. 12).

pG1Na was cut with SalI and XhoI. pBg was cut with NruI and XhoI, and an NruI/XhoI fragment containing the lac Z gene of pBg was cloned into the SnaBI site of pGO. Also cloned into pGO 5' to the lac Z gene was a BamHI-HindIII fragment containing the SV40 promoter from pLNSX (FIG. 13). The resulting plasmid is pGOSvBg (FIG. 14). pGOSvBg was then cut with SalI and XhoI, and SalI-XhoI fragment containing an SV40 promoter and a B-galactosidase gene was ligated into the SalI/XhoI digested pG1Na to form pG1NaSvBg. (FIG. 15). pG1 was cut with HindIII and SalI. pSvNa (FIG. 16), which contains the SV40 promoter from pLNSX and the neo Rgene from pN2, was also cut with HindIII and SalI, and a HindIII-SalI fragment containing an SV40 promoter and a β-galactosidase gene was ligated into HindIII/SalI digested pG1to form pG1XSvNa (FIG. 17).

Primers LacZ-3 and LacZ-4 were used to generate an 88 bp PCR fragment from SV40 DNA containing a sequence encoding the first 4 amino acids of the SV40 T-antigen and the core sequences of the nuclear-localizing signal (amino acids 127–147).

Primer LacZ-3 has the following sequence:
5'-CTG CTC TAG ATG GAT AAA GGT CCA AAA AAG AAG AGA AAG GTA GAA GAC CCC AAG G-3', SEQ ID NO:2

Primer LacZ-4 has the following sequence:
5'-ACT CAA AAA ACT TAG CAA TTC TGA AGG-3', SEQ ID NO:3

Primers LacZ-2 and LacZ-5 were used to generate an 833 bp PCR fragment from pG1NaSvBg containing a sequence encoding part of the SV40 nuclear localizing signal linked to amino acid number 6 of β-galactosidase.

Primer LacZ-2 has the following sequence:
5'-CCA CGC TCA TCG ATA ATT TCA CCG-3', SEQ ID NO:4

Primer LacZ-5 has the following sequence:
5'-TTG CTA AGT TTT TTG AGT GAT TCA CTG GCC GTC GTT TTA CAA CG-3', SEQ ID NO:5

Figure 18:
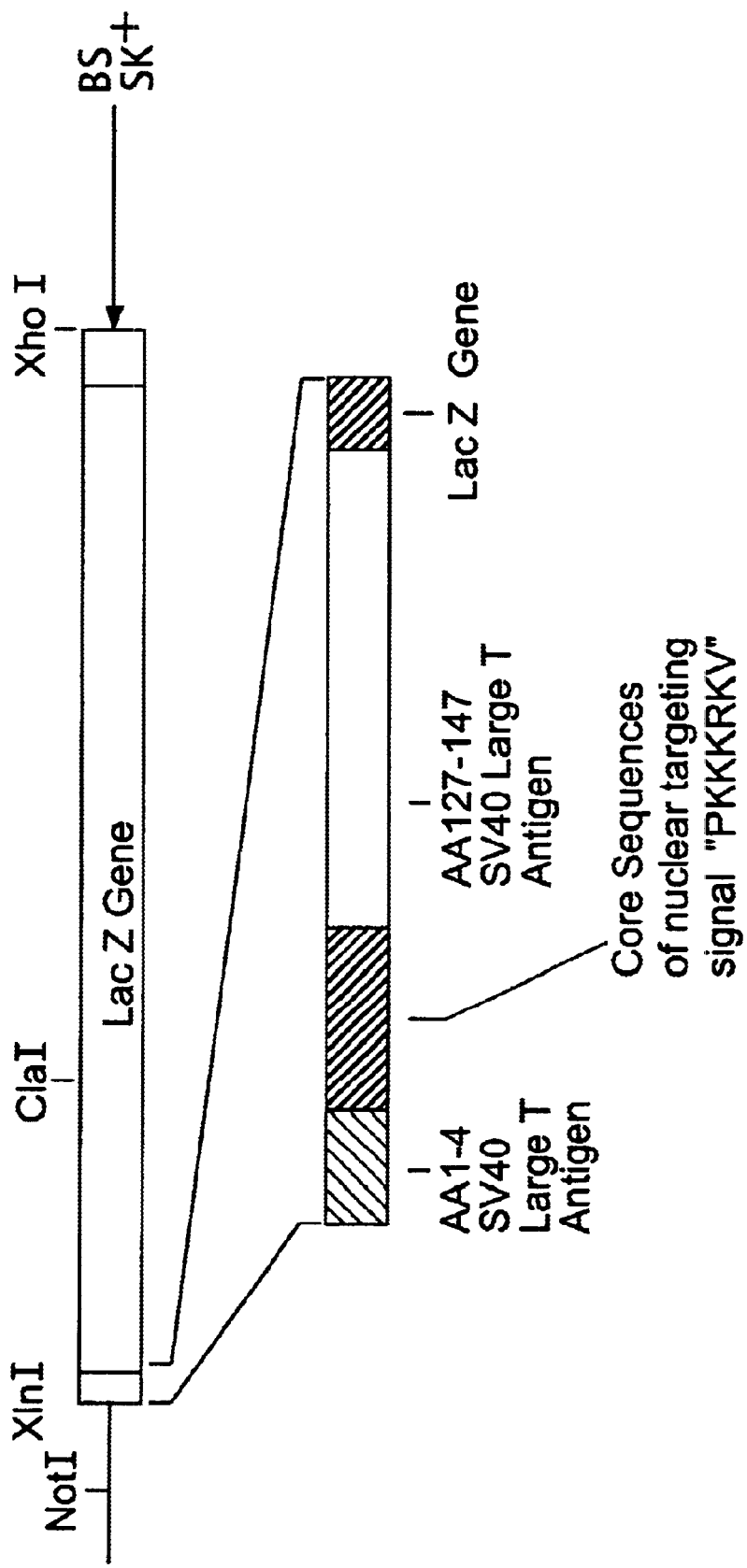
FIG. 18 is a map of the construct 5'-LacZ/BS SEQ ID NO: 8 is the core sequence of nuclear targeting signal.
Figure 19:
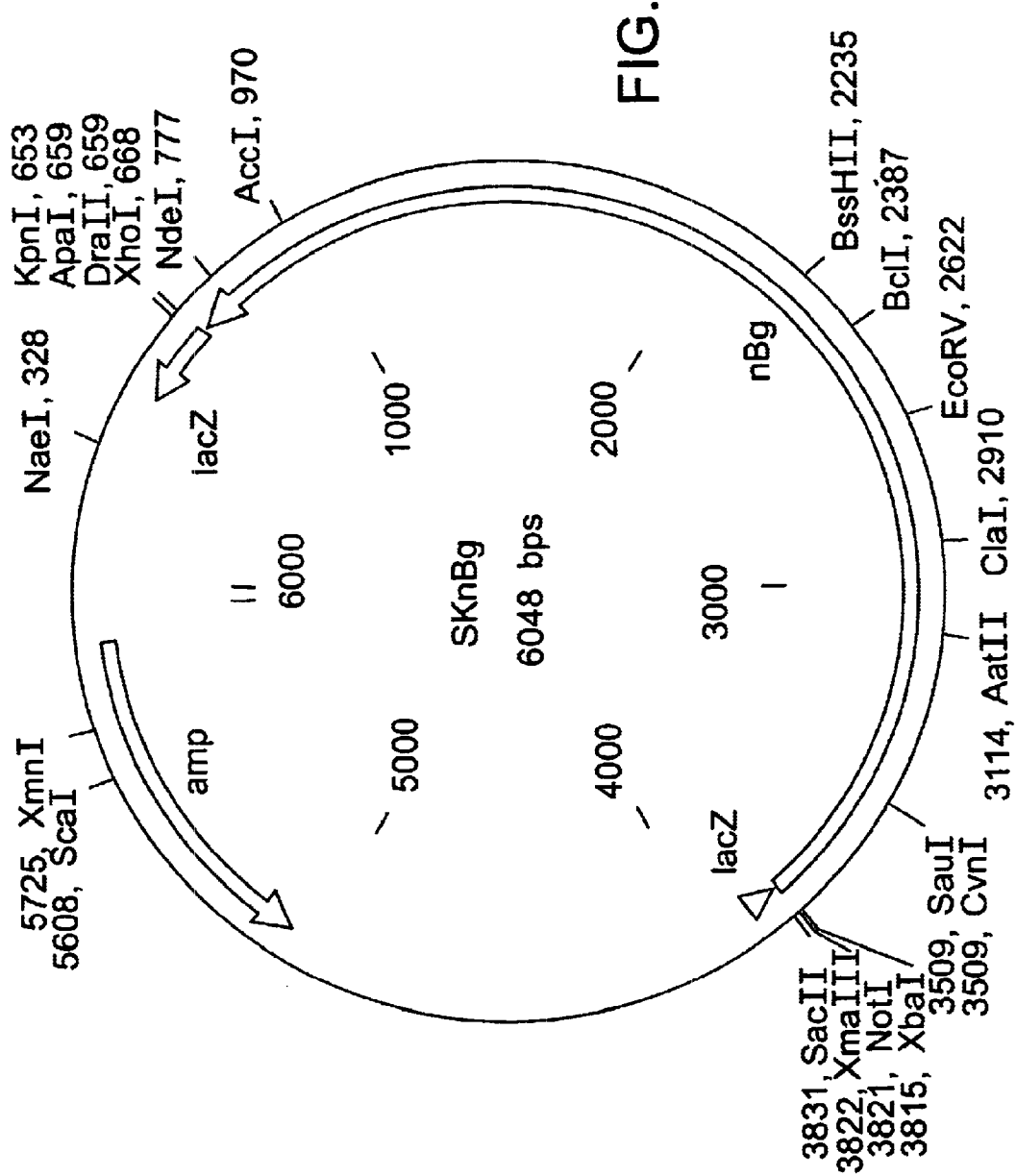
FIG. 19 is a map of plasmid pSKnBg.
Figure 20:
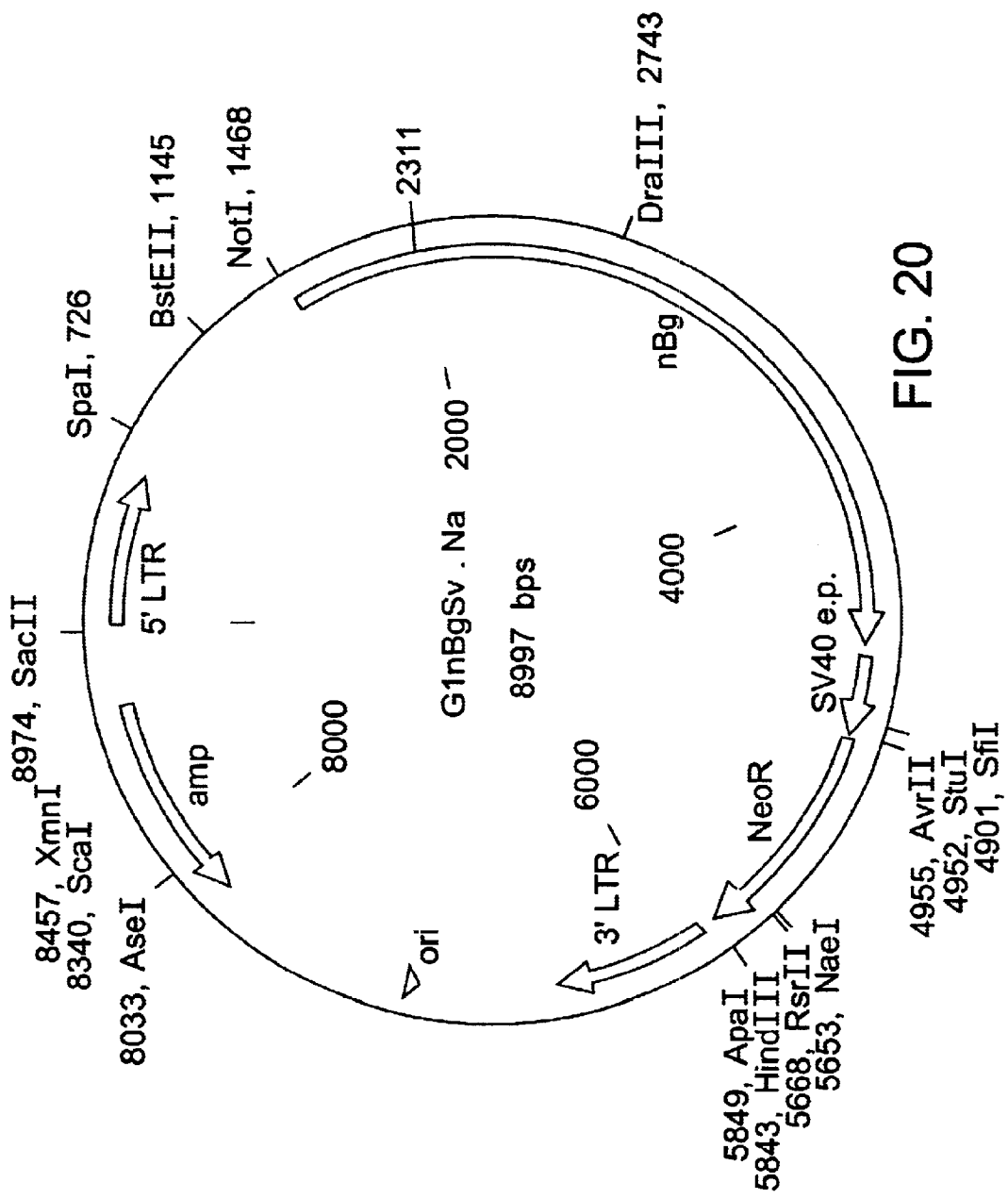
FIG. 20 is a map of plasmid pG1nBgSvNa.

The 88 bp PCR fragment and the 833 bp PCR fragment were mixed together, complementary end regions of these fragments were annealed, and the remainders of these fragments were filled in with DNA polymerase, resulting in an 894 bp fragment, which then was PCR-amplified with the terminal primers LacZ-2 and LacZ-3. The 894 bp fragment then was digested subsequently with XbaI and ClaI.

pBluescript I SK+ (Stratagene, LaJolla, Calif.) was digested with XbaI and ClaI, and the 894 bp fragment was ligated to the digested pBluescript I SK+ to form the intermediate construct designated 5'-LacZ/BS. (FIG. 18). 5'-LacZ/BS was digested with ClaI and XhoI, and ligated with a 2,242 bp 3'-terminal LacZ fragment from pG1NaSvBg to form the intermediate construct pSKnBg (FIG. 19.). pSKnBg then was digested with NotI and XhoI and ligated to pG1XSvNa which had been digested previously with NotI and SalI to form pG1nBgSvNa. (FIG. 20.). The 5' junction was sequenced for confirmation of the integrity of the translational reading frame.

pG1nBgSvNa was transduced into the PA317 amphotropic retrovirus packaging cell line (ATCC No. CRL 9078) (Miller, et al., *Mol. Cell. Biol.*, Vol. 6, pgs. 2895–2902

(1986); Miller, et al., *Biotechniques*, Vol. 7, pgs. 980–990 (1989)) to form the producer cell line PA317/G1nBgSvNa.

PA317/G1nBgSvNa producer cells ($2\times10^6$ cells) were grown in 1,700 cm$^2$ roller bottles at 32° C.

A two-day old supernatant was collected from the producer cells at 100% cell confluence.

The viral supernatant was harvested from the roller bottle by aspiration or pouring into a collection bottle. Immediately thereafter, the supernatant was clarified by pumping the supernatant through a 1.2$\mu$ nominal type polypropylene filter (Sartorius) to remove any debris and cells.

Vector supernatant from PA317/G1nBgSvNa producer cells was concentrated using the Millipore Pellicon tangential flow filtration system (Millipore, Bedford, Mass.) with a PLMK000C5 cassette (5 square feet, 300,000 NMWL). A pump was used to exert a low membrane feed pressure of 5 psi. Concentration was achieved within 30 minutes. To ensure high vector recovery, the surface area of the membrane was maximized and supernatant circulation was minimized with a low membrane feed pressure.

The concentrated viral supernatant (from about 100 ml to about 200 ml) was mixed with a $\frac{1}{12}$ volume of 4M NaCl on ice while stirring. Polyethylene glycol was added (8% w/v) slowly and stirred in ice for 3 hours. The precipitate was collected by centrifugation at 8,000×g for 15 minutes and resuspended in 0.01M tris (hydroxymethyl) aminomethane hydrochloride (TNE) pH7.5, 0.1M NaCl, and 0.001M ethylenediamine tetraacetic acid (i.e., at from about $\frac{1}{100}$ to $\frac{1}{25}$ of the original supernatant volume).

The suspension was layered on a discontinuous sucrose gradient (20% and 55% w/w) in TNE and centrifuged in a Beckman SW-40Ti rotor at 100,000×g for 2 hours at 20° C.

After the centrifugation, the sharp virus band was observed. The virus band was collected by inserting a 21-gauge hypodermic needle into the centrifuge tube, and diluted ten-fold with TNE and stored at −70° C.

Viral vector titer for G1nBgSvNa then was determined as follows:

On day 1, NIH-3T3 TK-cells were seeded at $1\times10^5$ cells/well of a six-well tissue culture plate (Becton Dickinson, Lincoln Park, N.J.) and incubated at 37° C. in 5% CO$_2$. On day 2, serial ten-fold dilutions of virus vector specimen in medium containing 8 $\mu$g/ml Polybrene were added to the target cells and incubated at 32° C. for an additional 24 hours. On day 3, the medium was removed and replaced with medium containing 800 $\mu$g/ml G418. Plates were incubated at 37° C. in 5% CO$_2$. On day 6, plates were refed with medium containing 400 ug/ml G418. On day 8, colonies were stained with methylene blue and the vector titer was calculated as the number of colony forming units (cfu) per ml.

Vector titer for the G1nBgSvNa virus generated from the PA317/G1nBgSvNa producer cell line as determined hereinabove was $1.8\times10^8$ colony forming units per ml. (CFU/ml). If desired, the vectors may be lyophilized, and then reconstituted prior to adminstration.

Example 3

Administration of Adenoviral and Retroviral Vectors to the Carotid Artery of Rats for Transduction of Endothelial Cells of Brain Vasculature Fischer rat 9L gliosarcoma cells were propagated in T-175 tissue culture flasks in Dulbecco's modified Eagle's medium (DMEM) with 10% fetal bovine serum (Hyclone Laboratories, Logan, Utah), 2 mM L-glutamine (Gibco BRL, Gaithersburg, Md.), 50 units/ml penicillin (Gibco), 50 $\mu$g/ml streptomycin (Gibco), and 2.5 $\mu$g/ml Fungizone (ICN Biomedicals, Inc., Costa Mesa, Calif.).

Eleven Fischer 344 rats, each weighing from 230 to 300 g, were anesthetized intraperitoneally with 90 mg/kg ketamine (Fort Dodge Laboratories, Inc., Fort Dodge, Iowa) and 10 mg/kg xylazine (Mobay Corporation, Shawnee, Kans.), and placed in a stereotaxic apparatus (David Kopf Instruments, Tujunga, Calif.). Syngeneic 9L gliosarcoma cells ($4\times10^4$ cells in 5 $\mu$l Hank's balanced salt solution) were injected into the deep white matter of the right cerebral hemisphere. 14 days later, the rats were reanesthetized, and an anterior midline neck incision was performed to expose the right carotid artery. The external carotid artery was ligated distally and a PE10 tube was cannulated through the stump of the external carotid artery into the common carotid artery. A 750 $\mu$l suspension of the adenoviral vector Av1LacZ4 containing $7.5\times10^9$ particles was infused over 1 minute into one group of 4 rats. A 750 $\mu$l suspension of the retroviral vector G1nBgSvNa containing $2.7\times10^7$ particles was infused over 1 minute into another group of 4 rats. A control group of 3 rats received saline. The stump of the external carotid artery was ligated, the cannula removed, and the rats allowed to recover. 48 hours later, the rats were sacrificed, and the heart perfused with 200 ml of heparinized saline (100 units/ml) to wash away residual blood. The brain was removed and trisected to isolate the tumor and the two cerebral hemispheres.

In order to increase the yield of harvested endothelial cells from the tissues, pools of the tumors, the perfused hemispheres, and the non-perfused hemispheres from all rats in each group of rats were formed. The specimens were minced into 3 mm pieces, and then underwent enzymatic digestion for 4 hours using 0.1% Type IV collagenase, 0.01% (Type V) hyaluronidase, and 0.002% Type V DNase (Sigma Chemical Co., St. Louis, Mo.). The digestion process was performed in RPMI complete media (RPMI1640, Gibco Laboratories, Grand Island, N.Y.), 4 mM L-glutamine (Gibco), 50 U/ml penicillin (Gibco), and 50 $\mu$g/ml streptomycin (Gibco). The cell suspension then was passed through a steel mesh screen, centrifuged at 400×g for 5 minutes, and resuspended in Hank's balanced salt solution. Debris and dead cells were removed using a lymphocyte separation media (Organon Teknika Cappel, Durham, N.C.) gradient (450×g for 20 minutes). The cells were washed twice in RPMI complete media (200×g for 5 minutes), and counted using a Neubauer hemocytometer (C. A. Hansser & Son, Philadelphia, Pa.). Viability was determined by Trypan blue exclusion.

The brain endothelial cells then were separated from the remainder of the pooled cells by immunomagnetic separation. (Jackson C. J., et al., *J. Cell Science* 96:257–62 (1990); George F, Brisson C. Poncelet P, et al, *Thrombosis and Hemostasis* 67:147–153 (1992). A commercially available mouse monoclonal IgG, antibody specific for rat brain and retinal endothelium, known as clone 4E8 (Harlan Bioproducts for Science, Indianapolis, Indiana) was attached to ferrous beads complexed to rat anti-mouse IgG$_1$. 120 micrograms of the mouse monoclonal IgG$_1$ antibody 4E8 was added to 120 mg of Dymal M-450 rat anti-mouse IgG$_1$ immunomagnetic beads (Dynal, Inc., Great Neck, N.Y.) in 4 ml of 5% BSA in PBS. After incubating for 60 minutes at room temperature, the antibody was decanted and the beads were washed with the BSA solution. The beads were brought up in 4 ml of the RPMI complete solution, and divided into eight 0.5 ml aliquots in 10 ml glass test tubes.

Cell suspensions from the digestion product of the tumors and cerebral hemispheres were added to the immunomagnetic bead solutions, and mixed by end-over-end rotation for 30 minutes at 4° C. A rare earth magnet then was applied to each solution for 10 minutes. The supernatant, which contained cells unattached to the magnetic beads, was separated and examined separately for gene transfer. The endothelial cells attached to the magnetic beads were washed with RPMI media and counted. In order to confirm that these cells were endothelial cells, phagocytosis of the beads by the endothelial cells was verified by phase-contrast microscopy, and the cells then were stained for von Willebrand's factor as described in Bacic F., et al., *Neurochemical Research* 17:699–702 (1992). In order to determine if 9L tumor cells would bind non-specifically to the immunomagnetic beads, a suspension of 9L cells was incubated with the immunomagnetic beads as hereinabove described, and then subjected to light microscopy and von Willebrand immunostaining.

β-galactosidase gene expression in endothelial cells after the intra-arterial infusion of the adenoviral vector Av1Lacz4 was determined by staining the endothelial cells from the tumor, the perfused hemisphere, and the non-perfused hemisphere with the X-gal histochemical technique described in Ram, et al., *Cancer Research*, Vol. 53, pgs. 83–88 (Jan. 1, 1993). Cells in 10 high-power fields (1,550±240, mean±SD of cells per sample) were counted using light microscopy, and the fraction of positive staining cells was recorded for each sample.

Endothelial cells from rats infused with the retroviral vector G1nBgSvNa were evaluated by quantitative analysis using the polymerase chain reaction (PCR). Genomic DNA was isolated from endothelial cells using SDS and proteinase K followed by phenol/Chloroform extraction and ethanol precipitation (Sambrook J; Fritsche E F, Maniatis T.: Molecular Cloning: A laboratory manual (2nd ed.). Cold Springs Harbor, N.Y.: Cold Spring Harbor Laboratory Press, 1989). Genomic DNA also was isolated from human SK-UT-1B cells (non-transduced human cell line) and mouse retroviral PA317/G1TKSvNa. 53 producer cells (Ram, et al., *J.Neurosurg.*, Vol. 84, pgs. 256–260 (1994)) that contain the $neo^R$ gene. For each sample, 1 μg of DNA from endothelial cells or from a standard curve consisting of mixtures of SK-UT-1B and PA317/G1TKSvNa.53 DNA's containing 0%, 0.01%, 0.03%, 0.1%, 0.3%, 1.0%, 3%, 10%, 30%, or 100% of DNA from PA317/G1TKSvNa.53 per/μg DNA (DNA content equivalent to 150,000 cells) were amplified by PCR under conditions as described in Otto, E., et al., *Hum. Gene Ther.* 5:567–575 (1994). After 27 cycles of successive incubations at 94° C. for 1 minute, 61° C. for 1.5 minutes, and 72° C. for 1 minute, 20 μl of each PCR reaction was electrophoresed on agarose gels. Southern blot hybridization analysis was performed with a $neo^R$ probe. Hybridization signals were quantified using a Phosphor Imager SF (Molecular Dynamics). The percentage of $neo^R$-containing cells in each sample was determined by interpolation of values obtained from the standard curve, assuming one proviral vector per transduced cell.

Estimation of gene transfer (X-gal staining after infusion of the adenoviral vector, PCR for $neo^R$ after retroviral vector infusion) was repeated on extravascular cells (tumor and brain cells) that were obtained from the supernatant of digested tissues after application of the magnet to separate the endothelial cells.

The percentage of endothelial cells transduced with the adenoviral vector or retroviral vector is given in Table I below.

TABLE I

| Fraction Tested | Initial Cell Count (×10$^7$) | Visability % | Bound Endothelial Cells (×10$^6$) | % Transduction of Endothelial Cells |
|---|---|---|---|---|
| AvILacZ4 vector | | | | |
| tumor | 20.0 | 95 | 100.0 | 1% |
| Ipsilateral (perfused) hemisphere | 3.0 | 87 | 8.0 | 0.8% |
| Contralateral (non-perfused) hemisphere | 1.6 | 88 | 16.0 | 0% |
| GInBgSvNa vector | | | | |
| tumor | 1.3 | 95 | 5.0 | 5.0% |
| Ipsilateral (perfused) hemisphere | 3.0 | 99 | 40.0 | 0.2% |
| Contralateral (non-perfused) hemisphere | 1.2 | 99 | 5.0 | 0% |

No X-gal positive cells were seen, and no $neo^R$ sequences were found after intra-carotid perfusion with saline. No vector sequences or gene expression were detected in non-endothelial cells of the brain or tumor after infusion of either adenoviral or retroviral vectors.

The above results demonstrate that a single intra-arterial infusion of adenoviral or retroviral particles results in significant transduction of endothelial cells located in blood vessels of a brain tumor.

The disclosure of all patents, publications, including published patent applications, database accession numbers, and depository accession numbers referenced in this specification are specifically incorporated herein by reference in their entirety to the same extent as if each such individual patent, publication, database accession number, and depository accession number were specifically and individually indicated to be incorporated by reference in its entirety.

It is to be understood, however, that the scope of the present invention is not to be limited to the specific embodiments described above. The invention may be practiced other than as particularly described and still be within the scope of the accompanying claims.

What is claimed is:

1. A method for inhibiting the growth of a brain tumor in a subject, comprising:

administering directly into a carotid artery or vertebral artery in close proximity to the brain tumor, a therapeutically effective amount of a replication-defective retroviral vector comprising a nucleic acid encoding a negative selective marker gene product that converts enzymatically an interacting agent into a cytotoxic agent, thereby selectively transfecting endothelial cells in the vaculature of the brain tumor and the negative selective marker is expressed in the endothelial cells; and administering the interacting agent to the vasculature of the brain tumor, wherein the negative selective marker gene product converts enzymatically the interacting agent to a cytotoxic agent, thereby destroying the endothelial cells in the vasculature of the brain tumor and inhibiting the growth of the brain tumor.

2. The method of claim 1, wherein the admninistration into the carotid artery or the vertebral artery is by angiography.

3. The method of claim 1, wherein the negative selective marker gene product is herpes simplex virus thymidine kinase, cytomegalovirus thymidine kinase, or varicella-zoster thymidine kinase.

4. The method of claim 3, wherein the interacting agent is ganciclovir, acyclovir, or 1-2-deoxy-2-fluoro-β-D-arbinofuransosil-5-indouracil.

* * * * *

UNITED STATES PATENT AND TRADEMARK OFFICE
CERTIFICATE OF CORRECTION

PATENT NO. : 6,669,935 B1
DATED : December 30, 2003
INVENTOR(S) : Oldfield et al.

It is certified that error appears in the above-identified patent and that said Letters Patent is hereby corrected as shown below:

Title page,
Item [56], References Cited, U.S. PATENT DOCUMENTS, -- 6,241,982 -- should be listed.
OTHER PUBLICATIONS, "Steg, P.G. et al" reference, "Steg, P.G. et al. Arterial gene transfer to rabbit endothelial and smooth muscle cells using perc utaneous delivary of an adenoviral vector. Circulation 90:1648-1656, 1994." should read -- Steg, P.G. et al. Arterial gene transfer to rabbit endothelial and smooth muscle cells using percutaneous delivery of an adenoviral vector. Circulation 90:1648-1656, 1994. --.
"Deonarain;" reference, "Deonarain; LIgand-targeted receptor-mediated vectorsd for gene delivery, 1998, Exp. Opin. Ther. Patents 8(1):53-69." should read -- Deonarain; Ligand-targeted receptor-mediated vectors for gene delivery, 1998, Exp. Opin. Ther. Patents 8(1):53-69. --.

Column 2,
Line 30, "Interferon-α, Interferon-β, and Interferon-α" should read -- Interferon-α, Interferon-β, and Interferon-γ --.

Column 11,
Line 35, "Ads" should read -- Ad5 --.

Column 13,
Line 41, "5'½mutated" should read -- 5'½ mutated --.
Line 46, "SV40 promoter The" should read -- SV40 promoter. The --.
Line 50, "1982) The" should read -- 1982). The --.

Column 14,
Line 16, "B-galactosidase" should read -- β-galactosidase --.
Line 17, "pG1NaSvBg. (FIG. 15)." should read -- pG1NaSvBg (FIG. 15). --.
Line 27, "digested pG1to form" should read -- digested pG1 to form --.

Column 18,
Table 1, "Visability" should read -- Viability --.
Table 1, "Bound Endothelial Cells (x10$^6$)" should read -- Bound Endothelial Cells (x10$^5$) --.

UNITED STATES PATENT AND TRADEMARK OFFICE
CERTIFICATE OF CORRECTION

PATENT NO. : 6,669,935 B1
DATED : December 30, 2003
INVENTOR(S) : Oldfield et al.

It is certified that error appears in the above-identified patent and that said Letters Patent is hereby corrected as shown below:

Column 18 (contd.),
Table 1, "GlnBgSvNa" should read -- G1nBgSvNa --.

Signed and Sealed this

Thirteenth Day of July, 2004

JON W. DUDAS
*Acting Director of the United States Patent and Trademark Office*

SEQUENCE LISTING

<160> NUMBER OF SEQ ID NOS: 8

<210> SEQ ID NO 1
<211> LENGTH: 13
<212> TYPE: DNA
<213> ORGANISM: Artificial Sequence
<220> FEATURE:
<223> OTHER INFORMATION: Kozak consensus sequence

<400> SEQUENCE: 1
gccgccacca tgg                                                        13

<210> SEQ ID NO 2
<211> LENGTH: 55
<212> TYPE: DNA
<213> ORGANISM: Artificial Sequence
<220> FEATURE:
<223> OTHER INFORMATION: Primer

<400> SEQUENCE: 2
ctgctctaga tggataaagg tccaaaaaag aagagaaagg tagaagaccc caagg          55

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
actcaaaaaa cttagcaatt ctgaagg                                         27

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
ccacgctcat cgataatttc accg                                            24

<210> SEQ ID NO 5
<211> LENGTH: 44
<212> TYPE: DNA
<213> ORGANISM: Artificial sequence
<220> FEATURE:
<223> OTHER INFORMATION: Primer

<400> SEQUENCE: 5
ttgctaagtt ttttgagtga ttcactggcc gtcgttttac aacg                      44

<210> SEQ ID NO 6
<211> LENGTH: 51
<212> TYPE: DNA
<213> ORGANISM: Artificial Sequence
<220> FEATURE:
<223> OTHER INFORMATION: Primer

<400> SEQUENCE: 6
aattcgcggc cgctacgtag tcgtaggatc cctcgagaag cttgggccca t              51

<210> SEQ ID NO 7
<211> LENGTH: 49

```
<212> TYPE: DNA
<213> ORGANISM: Artificial Sequence
<220> FEATURE:
<223> OTHER INFORMATION: Primer

<400> SEQUENCE: 7
gcgccggcga tgcatatgca tcctagggag ctcttcgaac ccgggtagc        49

<210> SEQ ID NO 8
<211> LENGTH: 7
<212> TYPE: PRT
<213> ORGANISM: Artificial Sequence
<220> FEATURE:
<223> OTHER INFORMATION: Nuclear targeting sequence

<400> SEQUENCE: 8

Pro Lys Lys Lys Arg Lys Val
1               5
```